(12) United States Patent
Damaser et al.

(10) Patent No.: US 9,782,440 B2
(45) Date of Patent: Oct. 10, 2017

(54) METHODS FOR TREATING GENITOURINARY DISORDERS

(71) Applicant: THE CLEVELAND CLINIC FOUNDATION, Cleveland, OH (US)

(72) Inventors: Margot S. Damaser, Cleveland Heights, OH (US); Charuspong Dissaranan, Ongkharak (TH); Howard B. Goldman, Beachwood, OH (US); Matthew Kiedrowski, Cleveland, OH (US); Marc S. Penn, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/770,221

(22) Filed: Feb. 19, 2013

(65) Prior Publication Data
US 2014/0079672 A1   Mar. 20, 2014

Related U.S. Application Data

(60) Provisional application No. 61/599,463, filed on Feb. 16, 2012, provisional application No. 61/640,974, filed on May 1, 2012.

(51) Int. Cl.
| | | |
|---|---|---|
| *A61K 35/22* | (2015.01) | |
| *A61K 35/28* | (2015.01) | |
| *C12N 5/0775* | (2010.01) | |
| *A61K 35/12* | (2015.01) | |

(52) U.S. Cl.
CPC ............ *A61K 35/28* (2013.01); *C12N 5/0663* (2013.01); *A61K 2035/124* (2013.01)

(58) Field of Classification Search
CPC .. A61K 2300/00; A61K 31/337; A61K 31/70; A61K 31/7088; A61K 9/0019; A61K 45/06; A61K 31/00; A61K 39/00; A61K 33/00; A61K 41/0004; A61K 9/007; A61K 9/08; A61K 9/1611; A61K 9/1641; A61K 9/1664; A61K 9/1688; A61K 9/19
USPC ................................. 424/93.7, 577
See application file for complete search history.

(56) References Cited

U.S. PATENT DOCUMENTS

| | | | |
|---|---|---|---|
| 7,118,746 B1 * | 10/2006 | Naughton ................ | A61K 8/02 424/184.1 |
| 2003/0181371 A1* | 9/2003 | Hunter .................... | A61L 27/24 514/17.2 |
| 2007/0265558 A1 | 11/2007 | Kleinbloesem et al. | |
| 2009/0123503 A1 | 5/2009 | Naughton et al. | |
| 2012/0276215 A1* | 11/2012 | Riordan ................ | A61K 9/0014 424/583 |
| 2012/0329154 A1* | 12/2012 | Moriya et al. ................ | 435/375 |

OTHER PUBLICATIONS

Temple University Health Systems. Male & Female Urinary Problems. Retrieved from the TUHS webpage on Jun. 12, 2014: <http://tuh.templehealth.org/content/urinary_problems.htm>.*
RightDiagnosis. Urinary Tract Infections. Retreived from the RightDiagnosis webpage on Jun. 12, 2014: <http://www.rightdiagnosis.com/u/urinary_tract_infections/intro.htm>.*
Krishna. Routes of Drug Administration. PharmacyFundas. Downloaded from the world wide web on May 1, 2013: <http://pharmacyfundas.com/routes-of-drug-administration/>.*
Drost, Adriana et al. In vitro Myogenic Differentiation of Human Bone Marrow-Derived Mesenchymal Stem Cells as a Potential Treatment for Urethral Sphincter Muscle Repair. Hematopoietic Stem Cells VII. Ann. NY Acad Sci 1176. 2009. pp. 135-143.*
Dissaranan, Charuspong et al. Stem Cell Therapy for Incontinence: Where are we now? What is the realistic potential?. Curr Urolo Rep (2011) 12. Springer Science + Business Media, LLC. pp. 336-344.*
Williams, J. Koudy et al. Cell versus Chemokine Therapy in a Nonhuman Primate Model of Chronic Intrinsic Urinary Sphincter Deficiency. The Journal of Urology. vol. 196, 1809-1815, Dec. 2016.*
Cruz et al., Pelvic Organ . . . Female Rats, Hindawi Publishing Corp., vol. 2012, Art. ID 612946, pp. 1-7.
Dissaranan, et al., Secreted Factors From Mesenchymal . . . , Glickman Urologic and Kidney Inst., Cleveland Clinic, 1-25.
Pires et al., "Unveiling the Differences of Secretome of Human Bone Marrow Mesenchymal Stem Cells, Adipose Tissue-Derived Stem Cells, and Human Umbilical Cord Perivascular Cells: A proteomic Analysis," Stem Cells and Development. 2016; 25(14): 1073-83.
Luo et al., "Role of Stromal-Derived Factor-1 in Mesenchymal Stem Cell Paracrine-Mediated Tissue Repair," Curr Stem Cell Res Ther. 2016; 11(7): 585-92.
Lau TT and Wang DA: "Stromal cell-derived factor-1 (SDF-1): homing factor for engineered regenerative medicine," Expert Opin Biol Ther. 2011; 11: 189.
Williams JK et al. "Cell versus Chemokine Therapy in a Nonhuman Primate Model of Intrinsic Urinary Sphincter Deficiency," Journal of Urology 2016; 196(6): 1809-15.
Williams JK et al. "Regenerative Medicine Therapies for Stress Urinary Incontinence," Journal of Urology. 2016; 196: 1619-26.
Langereis JD et al. Gelsolin expression increases β1-integrin affinity and L1210 cell adhesion. Cytoskeleton (Hoboken) 2013; 70:385-93.
Langereis, Jeroen D. "Neutrophil integrin affinity regulation in adhesion, migration, and bacterial clearance." Cell adhesion & migration 7.6 (2013): 486-491.

* cited by examiner

*Primary Examiner* — Scott Long
*Assistant Examiner* — Nghi Nguyen
(74) *Attorney, Agent, or Firm* — Tarolli, Sundheim, Covell & Tummino LLP

(57) ABSTRACT

One aspect of the present disclosure can include a therapeutic composition useful for treatment of a genitourinary disorder. The composition can be derived from a culture media having been in contact with a population of bone marrow-derived mesenchymal stem cells for a sufficient time period necessary to endow therapeutic activity in the culture media. The therapeutic property endowed to the culture media is the ability to promote structural and functional recovery of a dysfunctional organ or biological tissue associated with the genitourinary disorder.

7 Claims, 23 Drawing Sheets

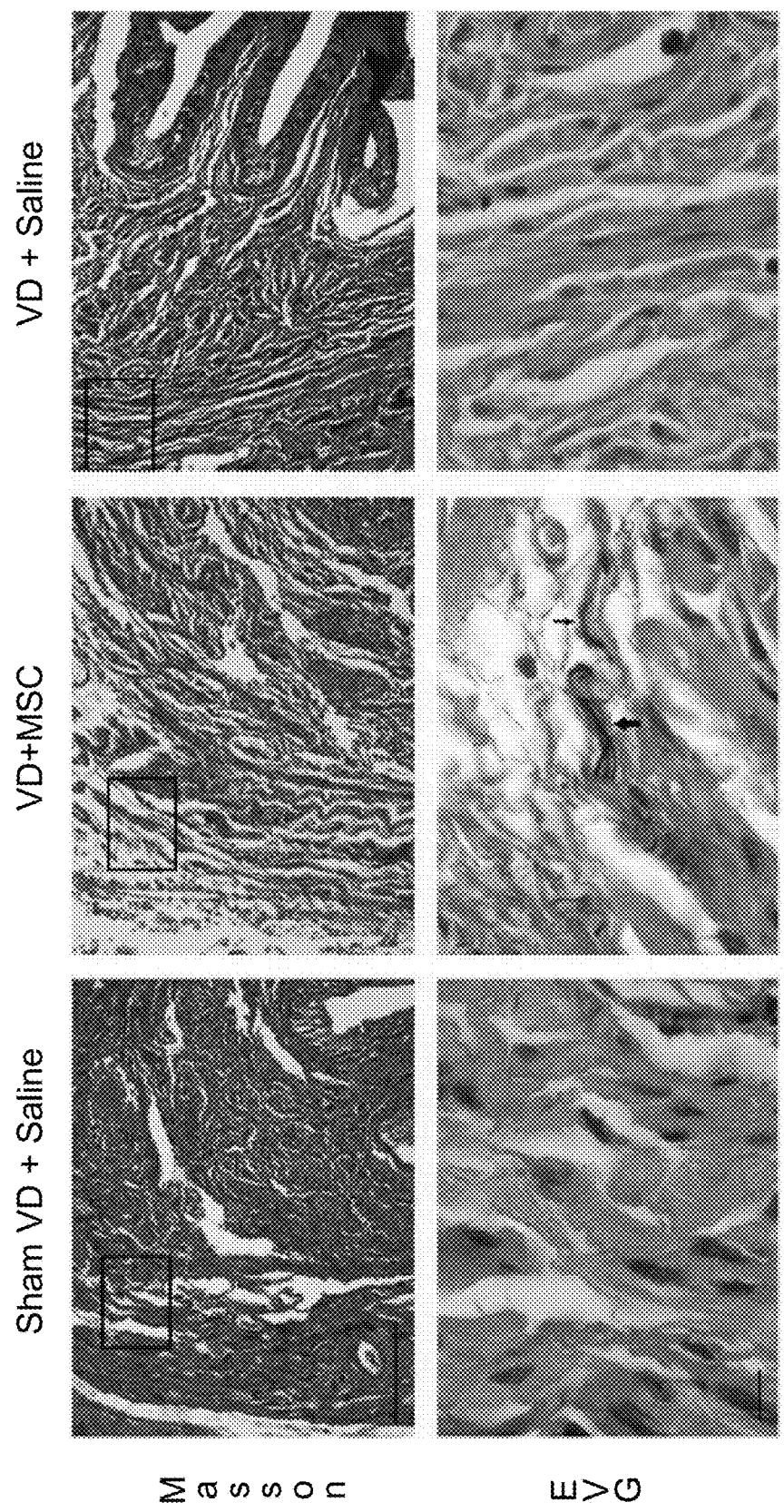

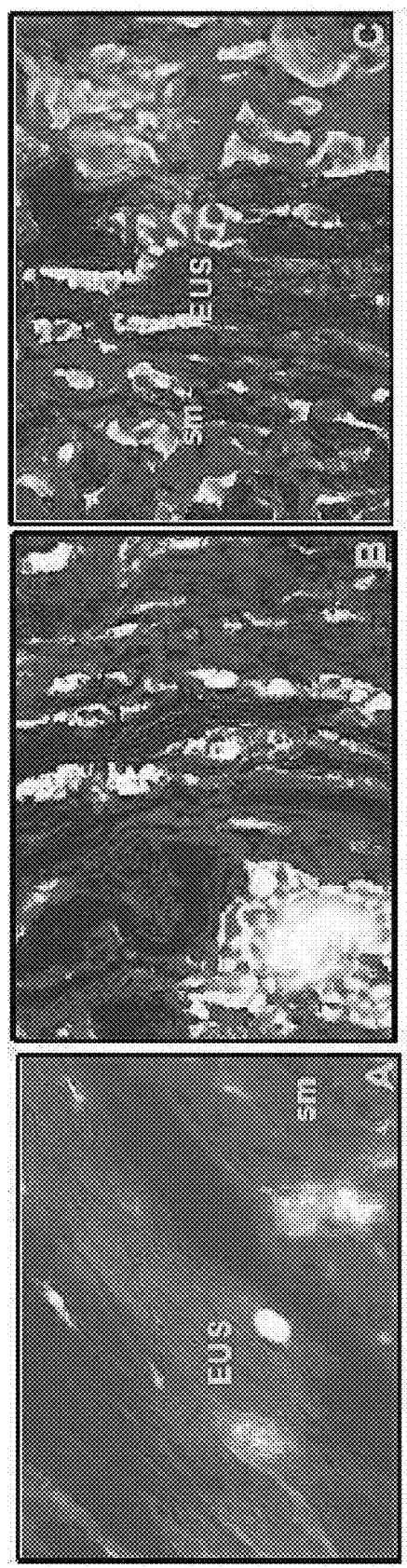

METHODS FOR TREATING GENITOURINARY DISORDERS

RELATED APPLICATIONS

This application claims the benefit of U.S. Provisional Patent Application Ser. Nos. 61/599,463, filed Feb. 16, 2012, and 61/640,974, filed May 1, 2012, the entirety of each of which is hereby incorporated by reference for all purposes.

TECHNICAL FIELD

The present disclosure relates generally to stem cells and methods for tissue repair and regeneration, and more particularly to mesenchymal stem cells, concentrated culture media therefrom, and related methods for treating or preventing genitourinary disorders, such as urethral and pelvic floor disorders.

BACKGROUND

Stress urinary incontinence (SUI) is a significant medical problem, with prevalence rates of 15-52% among women. Vaginal delivery has been correlated with development of SUI, likely via injury of the muscles and organs responsible for continence. Treatments include physiotherapy, continence pessaries, injectable bulking agents and surgery. Surgery remains the mainstay for cases that are nonresponsive to conservative measures. Although surgery can improve symptoms of SUI, it does not repair the underlying pathophysiology.

SUMMARY

In one aspect, the present disclosure can include a therapeutic composition useful for treatment of a genitourinary disorder. The composition can be derived from a culture media having been in contact with a population of bone marrow-derived mesenchymal stem cells (MSCs) for a sufficient time period necessary to endow therapeutic activity in the culture media. The therapeutic property endowed to the culture media is the ability to promote structural and functional recovery of a dysfunctional organ or biological tissue associated with the genitourinary disorder.

In another aspect, the present disclosure can include a method for treating or preventing a genitourinary disorder in a subject. One step of the method can include obtaining an effective amount of bone marrow-derived MSCs. A therapeutically effective amount of the bone marrow-derived MSCs can then be administered to the subject. At least a portion of the bone marrow-derived MSCs can home to a target location associated with the genitourinary disorder and promote a therapeutic effect via secretion of one or more paracrine factors.

Another aspect of the present disclosure can include a method for treating or preventing a genitourinary disorder in a subject. One step of the method can include culturing a population of bone marrow-derived MSCs. An amount of a concentrated culture media can then be obtained from the cultured population of bone marrow-derived MSCs. Next, a therapeutically effective amount of the concentrated culture media can be administered to the subject.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 3A is a series of flow cytometry results showing positivity for CD29, CD90, and CD54, as well as negativity for CD45. Blue is MSC at passage 8 (P8), 0.0139% of which were green fluorescent protein positive (GFP+) since this was prior to GFP-labeling. Red is MSC at P15, 90.1% of which were GFP+ after GFP-labeling. Green and orange are negative controls. 93.8% of P15 cells were CD29+, CD90+, CD54+ and CD45−. FIG. 3B shows adipogenic and osteogenic differentiation of MSC. Adipogenic-induced cells contained intracellular lipid droplets, stained orange by oil red O (scale bar=10 µm). Osteogenic-induced cells are red as assessed with Alizarin Red staining (scale bar=100 µm);

FIG. 1A shows ex vivo whole imaging results. Yellow oval indicates region of interest inside of which fluorescent flux was calculated. Pseudocolor scale indicates level of fluorescent flux with red being the most intense and purple being the least intense. FIG. 4B shows fluorescent flux of organs 1 week after VD or sham VD. Each bar indicates mean±standard error of the mean of organs from 9 rats. * indicates a statistically significant difference compared to the same organ from the sham VD group with $p<0.05$. ** indicates a statistically significant difference compared to the same organ from the sham VD group with $p<0.005$. FIG. 4C shows immunofluorescence from the urethra and vagina 1 week after VD or sham VD (blue indicates nuclei with DAPI stain, green indicates MSC labeled with GFP, and red indicates smooth muscle with α-actin immunolabeling). Rows 1-4 are at the same magnification (scale bar=100 µm). The last row shows an example immunofluorescence at higher magnification (scale bar=10 µm) demonstrating dual labeling of blue and green to show association of nuclei with MSCs. Rats that did not receive cells did not show fluorescence (data not shown);

FIG. 7A-B show urethral cross-sections stained with Masson's trichrome (upper panels) and near sections stained with elastin von Giesson stain (EVG; lower panels) one week after VD or sham VD and treatment with MSC or saline (FIG. 7A) or CCM or control media (FIG. 7B). Inset in upper panels indicates approximate area of higher magnification EVG example placed just below it. Note that anatomical structures do not align exactly in near sections. Scale bar for Masson's trichrome is 100 µm. Scale bar for EVG is 10 µm. Black arrows indicate disorganized elastin fibers in EVG examples;

FIG. 8A shows bladder pressure during LPP testing. FIG. 8B shows external urethral sphincter EMG amplitude during LPP testing. FIG. 8C shows external urethral sphincter EMG firing rate during LPP testing. Each bar indicates mean±standard error of the mean from 6-8 rats. * indicates a significant difference compared to the same outcome for the sham injured group with $p<0.05$;

FIG. 9A shows amplitude of PNSBP during clitoral brushing. FIG. 9B shows amplitude of PNSBP at baseline subtracted from amplitude during clitoral brushing (FIG. 9C). Note that the y-axis scaling in FIG. 9C is different than in FIG. 9A or FIG. 9B. FIG. 9D shows firing rate of PNSBP at baseline. FIG. 9E shows firing rate of PNSBP during clitoral brushing. FIG. 9F shows firing rate of PNSBP subtracted from amplitude during clitoral brushing. Note that the y-axis scaling in FIG. 9F is different than in FIGS. D-E. Each bar indicates mean±standard error of the mean from 5-8 rats. * indicates a significant difference compared to the same outcome for the sham VD&PNC group with $p<0.05$. + indicates a significant difference compared to the same outcome for the VD&PNC group treated with MSCs with $p<0.05$;

FIGS. 100A-C show examples of Masson's trichrome-stained transverse sections of the urethral showing urethral smooth muscle (sm) and the external urethral sphincter (EUS) 3 weeks after sham vaginal distension and pudendal nerve crush (VD&PNC) (FIG. 100A) and VD&PNC treated with saline (FIG. 10B) or MSCs (FIG. 10C);

DETAILED DESCRIPTION

Figure 1:
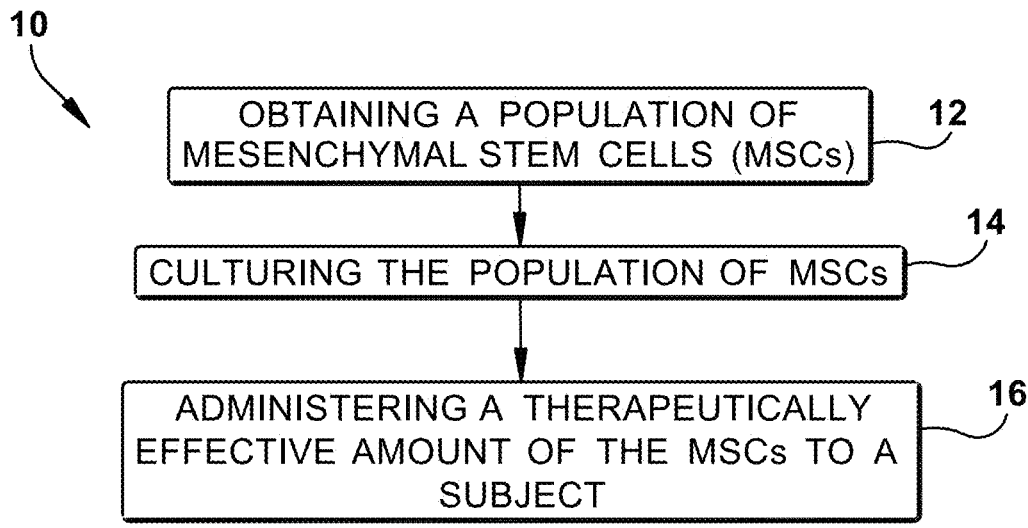
FIG. 1 is a process flow diagram illustrating a method for treating or preventing a genitourinary disorder in a subject according to one aspect of the present disclosure.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present disclosure pertains. Commonly understood definitions of molecular biology terms can be found in, for example, Rieger et al., *Glossary of Genetics: Classical and Molecular,* 5th Ed., Springer-Verlag: New York, 1991, and Lewin, *Genes V,* Oxford University Press: New York, 1994. The definitions provided herein are to facilitate understanding of certain terms used frequently herein and are not meant to limit the scope of the present disclosure.

In the context of the present disclosure, the term "genitourinary disorder" can include any infection, disease or other disorder that affects the normal function of the urinary and/or reproductive systems. Genitourinary disorders that may be treated according to the present disclosure can include, but are not limited to, overactive bladder, overactive bladder with sphincter dysfunction, urinary incontinence, urge urinary incontinence, stress urinary incontinence (SUI), Fowler's Syndrome, outlet obstruction, outlet insufficiency, pelvic hypersensitivity, sphincteric spasticity, detrusor hyperreflexia (neurogenic bladder), detrusor instability, benign prostatic hyperplasia, urethral stricture disease, tumors, interstitial (cell) cystitis, chronic pelvic pain syndrome, prostatodynia, prostatis, vulvodynia, vulvar vestibulitis, urethritis, and/or orchidalgia.

As used herein, the term "urethral disorder" can refer to any condition or disease characterized by urethral dysfunction in a subject. In some instances, a urethral disorder can include any condition in which there is a deviation from or interruption of the normal structure or function of the urethra. Non-limiting examples of urethral disorders can include urethral stricture and urethritis.

As used herein, the term "pelvic floor disorder" can refer to any condition or disease associated with the pelvic floor that results in weakening and/or injury to one or more of the muscles or connective tissue(s) that form the pelvic floor. In some instances, a pelvic floor disorder can occur when one or more muscles of the pelvic floor become weak, tight, or there is an impairment of the sacroiliac joint, lower back, coccyx, or hip joints. Non-limiting examples of pelvic floor disorders can include pelvic organ prolapse, urinary incontinence, and anal incontinence. Further examples of pelvic floor disorders are described below.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, aves, etc.), which is to be the recipient of a particular treatment. Typically, the terms "patient" and "subject" are used interchangeably herein in reference to a human subject.

As used herein, the terms "mesenchymal stem cell" or "MSC" can refer to a multipotent stem cell that can be derived from a variety of tissues and is capable of giving rise to connective tissue, bone, cartilage, and cells in the circulatory and lymphatic systems. MSCs can be found in the mesenchyme, the part of the embryonic mesoderm that consists of loosely packed, fusiform or stellate unspecialized cells. MSCs can be characterized by a number of surface markers, including expression of such markers as CD29, CD44, CD54, CD73, CD90, CD105, CD106, CD166 and STRO-1.

As used herein, the terms "effective", "effective amount", and "therapeutically effective amount" can refer to that amount of MSCs and/or concentrated culture media derived or obtained from MSCs that results in amelioration of symptoms or a prolongation of survival in a subject. A therapeutically relevant effect relieves to some extent one or more symptoms of a genitourinary disorder, or returns to normal either partially or completely one or more physiological or biochemical parameters associated with or causative of the genitourinary disorder.

As used herein, the terms "treating" or "treatment" of a genitourinary can include: (1) preventing at least one symptom of the genitourinary disorder, i.e., causing a clinical symptom to not significantly develop in a subject that may be exposed or predisposed to the disorder but does not yet experience or display symptoms of the disorder; (2) inhibiting the genitourinary disorder, i.e., arresting or reducing the development of the disorder and its symptoms; or (3) relieving the genitourinary disorder, i.e., causing regression of the disorder and its clinical symptoms.

As used herein, the term "therapeutic effect" can refer to an effect resulting from treatment of a subject that alters, prevents, improves or ameliorates the symptom(s) of a genitourinary disorder, or that cures a genitourinary disorder.

As used herein, the term "paracrine factor" can refer to a diffusible component produced by a first cell (e.g., a MSC) to affect another cell. A diffusible component can include any protein, growth factor, biomolecule, nutrient or fluid produced by the first cell.

As used herein, the term "conditioned medium" can refer to a formulation containing extracellular protein(s) and cellular metabolites, which has previously supported the growth of any desired eukaryotic cell type, such as bone-marrow derived MSCs.

As used herein, the term "population" when used with reference to MSCs can refer to one or more MSCs. In some instances, a population of MSCs can be isolated and then expanded and/or cultured ex vivo.

The present disclosure relates generally to stem cells and methods for tissue repair and regeneration, and more particularly to MSCs, concentrated culture media therefrom, and related methods for treating or preventing genitourinary disorders, such as urethral and pelvic floor disorders. The present disclosure is based, at least in part, on the discovery that: (1) bone marrow-derived MSCs injected into peripheral circulation in a rat model of SUI helped recovery of urethral structure and function; and (2) proteins secreted by the bone marrow-derived MSCs, when injected periurethrally, caused a similar degree of urethral recovery. Without wishing to be bound by theory, it is believed that the bone marrow-derived MSCs, upon administration, can home to the smooth muscle of a damaged organ or biological tissue (e.g., the urethra and vagina) and thereby facilitate functional and structural recovery of the damaged organ or biological tissue via secretion of paracrine factors. Based at least in part on the foregoing discovery, the present disclosure provides bone marrow-derived MSCs, concentrated culture media derived therefrom, and related non-invasive therapies for treating genitourinary disorders.

As shown in FIG. 1, one aspect of the present disclosure can include a method 10 for treating or preventing a genitourinary disorder (e.g., a urethral or pelvic floor disorder) in a subject. In some instances, the method 10 can include the following steps: obtaining a population of bone marrow-derived MSCs (Step 12); culturing the population of bone marrow-derived MSCs (Step 14); and administering a therapeutically effective amount of the bone marrow-derived MSCs to the subject (Step 16). Following administration, and as described in more detail below, at least a portion of the bone marrow-derived MSCs can home to a target location associated with the genitourinary disorder and promote a therapeutic effect via secretion of one or more paracrine factors.

In another aspect, the population of MSCs obtained at Step 12 can be derived from one or more sources, such as prenatal sources, postnatal sources, and combinations thereof. In some instances, tissues for deriving a suitable source of MSCs can include, but are not limited to, bone marrow. In other instances, the bone marrow-derived MSCs can be autologous, xenogeneic, allogeneic, and/or syngeneic. In one example, a population of MSCs can be derived from the bone marrow of a subject on which treatment will be performed, thereby preventing or mitigating rejection from the host. In some instances, MSCs derived from bone marrow can be obtained by extracting bone marrow from suitable long or flat bones. In other instances, flat bones may serve as the source of the MSCs as they contain more bone marrow. In further instances, the hip bone may serve as the source of MSCs.

Bone marrow can be extracted surgically. Various methods are commonly known in surgery to effect the extraction of bone marrow. In one example, bone marrow can be aspirated from a femur of a subject. In another example, bone marrow can be additionally or optionally aspirated from a tibia of a subject. In some instances, bone marrow can be aspirated by flushing the bone using a sterile solution (e.g., saline).

In another aspect, bone marrow-derived MSCs can be isolated and/or characterized following extraction using known techniques. The term "isolating" with reference to a particular component denotes separating that component from at least one other component of a composition from which the former component is thereby "isolated". Thus, in one example, the term "isolated" when used in relation to any bone marrow-derived MSC, group of bone marrow-derived MSCs, or a bone marrow-derived MSC population also implies that such bone marrow-derived MSC, group of bone marrow-derived MSCs, or bone marrow-derived MSC population does not form part of a subject.

In some instances, bone marrow-derived MSCs may be characterized by the presence of cell surface markers associated with specific epitopes (e.g., identified by antibodies) and/or the absence of certain cell surface markers (e.g., as identified by the lack of binding of specific antibodies). In other instances, isolation and/or characterization of bone marrow-derived MSCs may be confirmed by cell proliferation. In further instances, analysis of bone marrow-derived MSC markers may be performed using flow cytometric analysis, Western blot analysis, RT-PCR, in situ hybridization, immunoflourescence, immunohistochemistry, and the like. In one example, bone marrow-derived MSCs can be isolated or sorted for ICAM-1 using flow cytometry. Analysis of bone marrow-derived MSC proliferation may be performed using known methods, such as BrdU incorporation. Bone marrow-derived MSCs may also be identified by functional assays both in vitro and in vivo, particularly assays relating to the ability of cells to give rise to multiple differentiated progeny, assays for responsiveness to canonical WNT signaling, and the like.

In one example, markers that may be used to confirm isolation of bone marrow-derived MSCs (e.g., by FACS or other similar methods) can include Sca1, ABCG2, Sox9, Activin, Oct4, Bmi1, Hand1, IGF2, MTS1, Col1, Col3, Col15, Col18, Prolyl hydroxylase, and Stella. In another example, markers that may be used to confirm isolation of bone marrow-derived MSCs can include CD29, CD54, CD90 but not CD45.

In another aspect, an isolated population of bone marrow-derived MSCs can be cultured at Step 14. Appropriate culture media and culture conditions for culturing and expanding bone marrow-derived MSCs are known in the art. In some instances, the terms "expanding" and "expansion" can refer to substantially differentiationless maintenance of bone marrow-derived MSCs and ultimately cell growth, i.e., increase of a cell population (e.g., at least 2-fold) without differentiation accompanying such increase. In one example, bone marrow-derived MSCs can be cultured in serum-free DMEM for a desired period of time (e.g., about 24 hours) before passaging the cells. In another example, bone marrow-derived MSCs can be cultured in serum-free DMEM/high-glucose supplemented with N2 and B27 solutions and growth factors. In some instances, bone marrow-derived MSCs can be incubated at about 37° C. in about 5% $CO_2$ in tissue culture treated wells. In other instances, bone marrow-derived MSCs can be cultured in the presence of feeder cells. In further instances, bone marrow-derived MSCs can be briefly cultured in hypoxic conditions (e.g., 0.1% to 10% oxygen, such as about 5% oxygen) to upregulate production of a desired protein or proteins. Specific culture conditions are readily determined and adjusted by one of ordinarily skill in the art.

Either before, during, or after expanding a population of bone marrow-derived MSCs, one or more of the bone marrow-derived MSCs may be engineered to express a target gene product, which may impart a wide variety of functions, such as improved properties in expressing proteins resembling physiological reactions or increased expression of a particular protein useful for a specific application. Generally speaking, methods that may be useful to genetically engineer bone marrow-derived MSCs are known in the art (see, e.g., U.S. Patent Publication No. 2007/0077232 A1). In some instances, bone marrow-derived MSCs may be engineered to express a target gene product that is biologically active and which: provides a chosen biological function; acts as a reporter of a chosen physiological condition; augments deficient or defective expression of a gene product; or provides an anti-viral, anti-bacterial, anti-microbial, or anti-cancer activity. In other instances, a target gene product may be a peptide or protein, such as an enzyme, hormone, cytokine, antigen, or antibody, a regulatory protein, such as a transcription factor or DNA binding protein, or a structural protein, such as a cell surface protein. In other instances, a target gene product may be a nucleic acid, such as a ribosome or antisense molecule. In further instances, a target gene product can include a gene product (or products) that enhance cell growth.

In one example, one more bone marrow-derived MSCs can be engineered to overcome or compensate for a genitourinary disorder (e.g., pelvic organ prolapse) in a subject that is genetically predisposed to the disorder. In this case, one or more bone marrow-derived MSCs can be engineered to express an increased or decreased amount of particular protein (or proteins) that may be causative of, or contribute to, the disorder.

In another aspect, a therapeutically effective amount of bone marrow-derived MSCs can be administered to the subject (Step 16). Prior to administration, the bone marrow-derived MSCs can be formulated into pharmaceuticals in the form of capsules, injectables, hydrogels, or into any other appropriate formulation known to one of skill in the art. Liquid preparations may take the form of, for example, solutions, syrups, suspensions, or other suitable vehicles before use. Such liquid preparations may be prepared by conventional means with pharmaceutically acceptable additives, such as suspending agents or emulsifying agents. Pharmaceutical formulations may be delivered to the subject via a variety of routes using standard procedures. For example, such delivery may be site-specific, oral, nasal, intravenous, subcutaneous, intradermal, transdermal, intramuscular or intraperitoneal.

Upon administering the bone marrow-derived MSCs to a subject, all or only a portion of the bone marrow-derived MSCs can home to a target location associated with the genitourinary disorder. A target location can include any one or combination of biological tissue(s) or organ(s) associated with a genitourinary disorder. Non-limiting examples of biological tissues can include bone, muscle (e.g., smooth muscle), connective tissue, nerve tissue (e.g., pudendal nerve) and fat. In some instances, the target location can include a biological tissue or organ that is diseased, dysfunctional, or otherwise abnormal as a result of the genitourinary disorder. In other instances, the target location can include a biological tissue or organ located some distance (e.g., substantially adjacent) from a diseased, dysfunctional, or otherwise abnormal biological tissue or organ.

Administered bone marrow-derived MSCs can home to the target location by one or more mechanisms. In some instances, bone marrow-derived MSCs can home to the target location as a result of cell surface markers and/or soluble factors (e.g., proteins) that are uniquely expressed and/or secreted on or from a diseased, dysfunctional, or otherwise abnormal biological tissue(s) or organ(s) associated with the genitourinary disorder. In other instances, administered bone marrow-derived MSCs can home to the target location as a result of cell surface markers and/or soluble factors that may be expressed and/or secreted on or from biological tissue(s) or organ(s) some distance from the diseased, dysfunctional, or otherwise abnormal biological tissue(s) or organ(s). In further instances, administered bone marrow-derived MSCs can be engineered to express molecules (e.g., proteins) that preferentially bind to receptors associated with cells at the target location.

Once the administered bone marrow-derived MSCs have homed to the target location, the bone marrow-derived MSCs can secret one or more paracrine factors (e.g., cytokines and growth factors). Release of paracrine factors at the target site can promote a therapeutic effect by inducing repair and regeneration of a diseased, dysfunctional, or otherwise abnormal biological tissue or organ associated with the genitourinary disorder. Repair and regeneration may occur through any one or combination of mechanisms, such as neovascularization, diminished inflammatory response, activation of resident stem cells, and MSC differentiation. Advantageously, the method 10 can promote structural and functional recovery of biological tissue(s) and/or organ(s) comprising the target site via paracrine factors, thereby providing a noninvasive approach to treating a variety of genitourinary disorders.

As noted above, the method 10 can be used to treat or prevent a variety of genitourinary disorders. Further examples of genitourinary disorders treatable by the method 10 can include interstitial cystitis/painful bladder syndrome, incontinence as a result of prostatectomy, erectile dysfunction, urinary incontinence, and fecal incontinence. In one example, the method 10 can be used to treat SUI caused by childbirth. SUI is thought to result from various muscle, soft tissue, and nerve injuries to the urethra and pelvic floor. The most common cause of SUI is vaginal delivery. Ultimately, the urethra is unable to maintain adequate function and leakage occurs when there are sudden rises in abdominal pressure.

To treat the subject, MSCs can first be harvested from a source of bone marrow of a post-partum subject (either before or after child birth). Bone marrow-derived MSCs that are CD45−, CD29+, CD54+, and CD90+ can then be isolated and expanded in culture. For instance, bone marrow-derived MSCs can be cultured in serum-free DMEM for about 24 hours in a normoxic incubator with about 5% $CO_2$ at about 37° C. Following expansion, an effective amount of the bone marrow-derived MSCs can be intravenously administered to the subject after a period of time following child birth. It should be appreciated, however, that an effective amount of bone marrow-derived MSCs can alternatively or additionally be administered to the subject prior to child birth. In one example, the bone marrow-derived MSCs can be administered to the subject immediately after child birth. In another example, the period of time following childbirth and until administration can be hours, days, weeks or months.

Following administration, the bone marrow-derived MSCs can home to the urethra and vagina of the subject as a result of increased CCL7 levels, which can be up-regulated in the urethra and vagina after vaginal distension. Once the bone marrow-derived MSCs have homed to the urethra and vagina, the cells can secret one or more paracrine factors. As discussed above, secretion of paracrine factors can induce repair and regeneration of damaged tissue(s) and/or organ(s). In some instances, secretion of paracrine factors can promote recovery of damaged smooth muscle cells, which may lead to improved urethral structure and function and, thus, improved continence in the subject.

Figure 2:
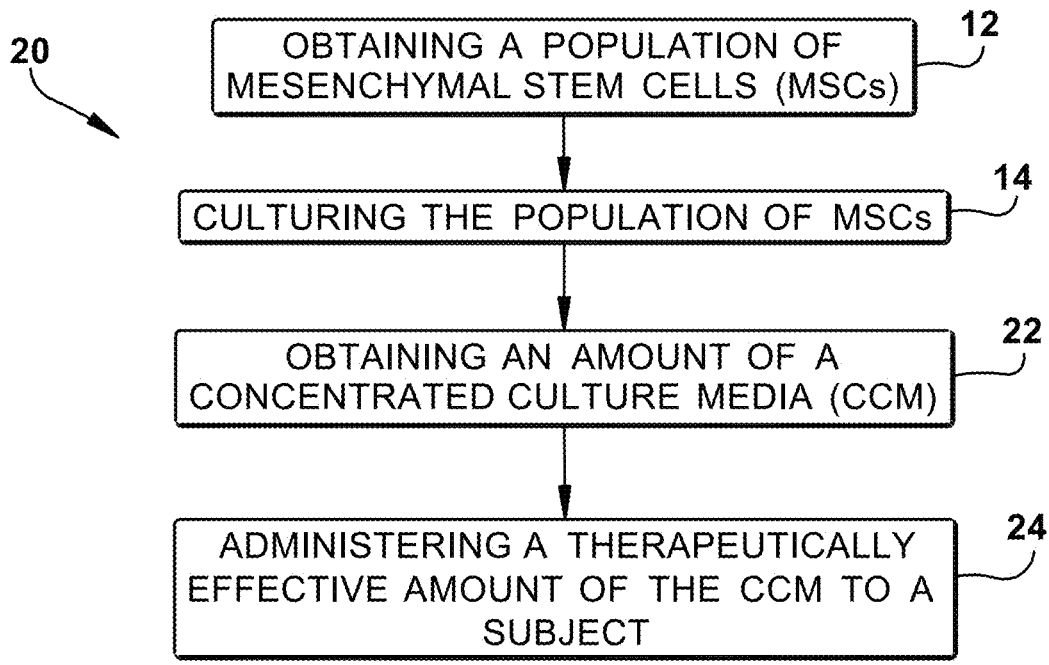
FIG. 2 is a process flow diagram illustrating a method for treating or preventing a genitourinary disorder in a subject according to another aspect of the present disclosure.

Another aspect of the present disclosure is illustrated in FIG. 2 and includes a method 20 for treating or preventing a genitourinary disorder (e.g., a urethral or pelvic floor disorder) in a subject. Steps of the method 20 similar or identical to those of the method 10 in FIG. 1 use the same reference numbers. The method 20 (FIG. 2) generally includes the steps of: obtaining a population of bone marrow-derived MSCs (Step 12); culturing the population of bone marrow-derived MSCs (Step 14); obtaining an amount of a concentrated culture media (Step 22); and administering a therapeutically effective amount of the concentrated culture media to a subject suffering from a genitourinary disorder (Step 24).

In one aspect, the method 20 can include obtaining a population of bone marrow-derived MSCs (Step 12). As discussed above, a population of autologous bone marrow-derived MSCs can be obtained from a source of bone marrow, such as a flat bone or hipbone. The use of bone marrow-derived MSCs for treating certain genitourinary disorders, such as SUI is advantageous over MSCs obtained from other sources, i.e., autologous muscle because obtaining MSCs from an autologous muscle source requires a muscle biopsy followed by a tedious process of expanding the number of available cells. Bone marrow-derived MSCs, on the other hand, can be readily obtained and expanded as described herein.

Following extraction, the population of bone marrow-derived MSCs can be isolated and/or characterized using known techniques. In some instances, bone marrow-derived MSCs can be characterized by the presence and/or absence of cell surface markers. In other instances, isolation and/or characterization of bone marrow-derived MSCs may be confirmed by cell proliferation. In further instances, bone marrow-derived MSCs can be isolated and/or characterized by functional assays both in vitro and in vivo. In one example, markers that may be used to confirm isolation of bone marrow-derived MSCs can include CD29, CD54, CD90 but not CD45.

In another aspect, a population of bone marrow-derived MSCs can be cultured at Step 14. The bone marrow-derived MSCs can be cultured in any medium that adequately addresses the nutritional needs of the cells being cultured. Examples of cell media include, but are not limited to DMEM, Ham's F12, RPMI 1640, Iscove's, McCoy's, and other media formulations readily apparent to those skilled in the art, such as those found in *Methods For Preparation of Media, Supplements and Substrate For Serum-Free Animal Cell Culture* Alan R. Liss, New York (1984) and *Cell & Tissue Culture: Laboratory Procedures*, John Wiley & Sons Ltd., Chichester, England 1996, both of which are incorporated by reference herein in their entirety. The medium may be supplemented with any components necessary to support the desired cell culture. Additionally serum, such as bovine serum, which is a complex solution of albumins, globulins, growth promoters and growth inhibitors may be added if desired. The serum should be pathogen-free and carefully screened for mycoplasma, bacterial, fungal, and viral contamination.

Other ingredients, such as vitamins, growth and attachment factors, proteins, etc., can be selected by those of skill in the art in accordance with a particular need or application. In some instances, genetically engineered bone marrow-derived MSCs may be cultured. Such cells can be modified, for example, to express a desired protein or proteins so that the concentration of the expressed protein (or proteins) in the medium is optimized for the particular desired application. Further ingredients that may be included in the culture media can include, but are not limited to: amino-acids (both D and/or L-amino acids), such as glutamine, alanine, arginine, asparagine, cysteine, glutamic acid, glycine, histidine, isoleucine, leucine, lysine, methionine, phenylalanine, proline, serine, threonine, tryptophan, tyrosine, valine, and their derivatives; acid soluble subgroups, such as thiamine, ascorbic acid, ferric compounds, ferrous compounds, purines, glutathione and monobasic sodium phosphates; sugars; deoxyribose; ribose; nucleosides; water soluble vitamins; riboflavin; salts; trace metals; lipids; acetate salts; phosphate salts; HEPES; phenol red; pyruvate salts and buffers; fat soluble vitamins (including A, D, E and K); steroids and their derivatives; cholesterol; fatty acids and lipids; Tween 80; 2-mercaptoethanol pyrimidines; as well as a variety of supplements including serum (fetal, horse, calf, etc.), proteins (insulin, transferrin, growth factors, hormones, etc.) antibiotics (gentamicin, penicillin, streptomycin, amphotericin B, etc.) whole egg ultra filtrate, and attachment factors (fibronectins, vitronectins, collagens, laminins, tenascins, etc.).

The bone marrow-derived MSCs can be cultured to produce a conditioned media. A conditioned media can include a formulation containing extracelluar protein(s) and cellular metabolites, which has previously supported the growth of any desired eukaryotic cell type, such as bone marrow-derived MSCs. Conditions under which the bone marrow-derived MSCs can be cultured to obtain conditioned media are discussed above. Generally, the bone marrow-derived MSCs can be cultured by any means known in the art. In some instances, the bone marrow-derived MSCs can be cultured in an environment that enables aseptic processing and handling. In other instances, the media can be conditioned in a manner allowing for large scale growth (yielding large scale conditioned media). In one example, 100% confluent bone marrow-derived MSCs can incubated in serum-free DMEM for about 24 hours in a normoxic incubator with about 5% $CO_2$ at about 37° C. to produce the conditioned media. When appropriate (i.e., once the medium is conditioned so that extracellular proteins, such as growth factors have reached desirable levels in the medium), the conditioned medium (e.g., the supernatant) can be extracted using known extraction techniques.

At Step 22, an amount of concentrated culture media can be obtained following extraction of the conditioned media. In some instances, the conditioned media can be subjected to centrifugation to produce the concentrated culture media. In one example, the conditioned media can be concentrated at least about 10-fold to about 100-fold. In another example, the conditioned media can be concentrated about 50-fold. In one example, the conditioned media can be centrifuged at about 4,000 rpm for about 45 minutes to obtain a 50× concentrated culture media. The concentrated culture media can be subject to further processing, such as sterile filtering using a micron filter (e.g., a 0.22 μm filter). Depending upon particular culture conditions, the concentrated culture media can contain any number of paracrine factors. Non-limiting examples of paracrine factors that may be present in the concentrated culture media can include those listed in Table 1 (below). It should be understood, however, that the list of factors in Table 1 is not an exhaustive list of factors, and is provided solely to further characterize the concentrated culture media.

At Step 24, a therapeutically effective amount of the concentrated culture media can be administered to the subject. The concentrated culture media can be formulated into a pharmaceutical composition in the form of capsules, injectables, hydrogels, or any other appropriate formulation known to one of skill in the art (discussed above). It will be appreciated that the concentrated culture media can be combined with other components or materials for therapeutic applications, such as a bandage (e.g., an adhesive or non-adhesive bandage) or with polymerizable or cross-linking hydrogels. The pharmaceutical formulation may be delivered to the subject via a variety of routes using standard procedures. For example, delivery may be site-specific, oral, nasal, intravenous, subcutaneous, intradermal, transdermal, intramuscular or intraperitoneal.

In another aspect, the concentrated culture media can be administered to the subject at a target location associated with the genitourinary disorder. Examples of target locations are described above. In some instances, the concentrated culture media can be directly injected at the target location. In other instances, the concentrated culture media can be injected at a distance (e.g., substantially adjacent, peripheral to, or surrounding) from the target location. Administering the concentrated culture media can promote a therapeutic effect by inducing repair and regeneration of a diseased, dysfunctional, or otherwise abnormal biological tissue and/or organ associated with the genitourinary disorder. Repair and regeneration may occur through any one or combination of mechanisms, such as neovascularization, diminished inflammatory response, and activation and/or differentiation of resident stem cells.

Advantageously, the method 20 can promote structural and functional recovery at the target site via a paracrine effect, which provides a noninvasive approach to treating a variety of genitourinary disorders. The discovery of the present disclosure that proteins secreted by bone marrow-derived MSCs can elicit the same functional improvement as seen with MSC administration provides additional advantages. For instance, instead of performing a muscle biopsy and then expanding the obtained MSCs, it is now possible to synthetically create the appropriate paracrine factors, or have a bank of bone marrow-derived MSCs producing such paracrine factors. This composition could then be packaged and utilized when necessary without worrying about MSC differentiation into unwanted cell lines or neoplasms. Thus, in another aspect, the present disclosure can include a therapeutic composition of concentrated culture media produced by the method 20 described above.

The method 20 can be used to treat or prevent a variety of the genitourinary disorders, such as urethral and pelvic floor disorders. In one example, the method 20 can be used to treat SUI caused by childbirth. To do so, MSCs can be harvested from a source of bone marrow in a post-partum subject (either before or after child birth). Bone marrow-derived MSCs that are CD45−, CD29+, CD54+, and CD90+ can then be isolated and expanded in culture. For instance, bone marrow-derived MSCs can be cultured in serum-free DMEM for about 24 hours in a normoxic incubator with about 5% $CO_2$ at about 37° C. Following expansion, conditioned media (e.g., supernatant) can be extracted and centrifuged at about 4,000 rpm for about 45 minutes to obtain an amount of 50× concentrated culture media. If desired, the concentrated culture media can be sterilized using a 0.22 μm filter.

An effective amount of the concentrated culture media can be administered to the subject after a period of time following child birth. For example, an effective amount of the concentrated culture media can be injected into the subject at a periurethral location. It should be appreciated that the concentrated culture media can alternatively or additionally be administered to the subject prior to child birth. In one example, the concentrated culture media can be administered to the subject immediately after child birth. In another example, the period of time until administration of the concentrated culture media can be hours, days, weeks or months. As discussed above, delivery of the concentrated culture media, which contains one or more paracrine factors can induce repair and regeneration of damaged urethral and vaginal tissue. In some instances, the presence of paracrine factors in the concentrated culture media can promote recovery of damaged smooth muscle cells, which may lead to improved continence in the subject.

Another aspect of the present disclosure can include a therapeutic composition useful for treatment of a genitourinary disorder. The composition can be derived from a culture media having been in contact with a population of bone marrow-derived MSCs for a sufficient time period necessary to endow therapeutic activity in the culture media. The therapeutic property endowed to the culture media is the ability to promote structural and functional recovery of a dysfunctional organ or biological tissue associated with the genitourinary disorder.

In some instances, the culture media can be obtained from media (e.g., conditioned media) that previously supported the growth of the bone marrow-derived MSCs. For example, the culture media can be obtained according to the method 20 described above.

In some instances, the culture media can be concentrated (e.g., in volume). In one example, the culture media can be concentrated at least about 10×. In another example, the culture media can be concentrated at least about 50×. In other instances, the culture media can be concentrated and used for the formulation of a pharmaceutical. Techniques for formulating culture media (e.g., concentrated culture media) as a pharmaceutical are described above. Further examples of techniques and compositions for formulating culture media as a pharmaceutical are disclosed in U.S. Patent Publication No. 2012/0276215 A1.

In some instances, the population of bone-marrow derived MSCs can be an isolated population. The term "isolated" can indicate that a MSC or population of MSCs to which it refers is not within its natural environment. The MSC or population of MSCs has been substantially separated from surrounding tissue. In one example, the MSC or population of MSCs is substantially separated from surrounding tissue if the sample contains at least about 75%, at least about 85%, at least about 90%, or at least about 95% bone marrow-derived MSCs. In other words, the sample is substantially separated from the surrounding tissue is the sample contains less than about 25%, less than about 15%, or less than about 5% of materials other than the MSCs. Such percentage values can refer to percentage by weight. The term "isolated" can encompass MSCs that have been removed from the subject from which they originated, and exist in culture.

In some instances, the culture media that previously supported the growth of the population of bone marrow-derived MSCs can be obtained from a substantially pure population of bone marrow-derived MSCs. A "substantially pure population" can refer to a population of bone marrow-derived MSCs that contains at least 99% MSCs. Cell purification can be accomplished by any means known to one of ordinary skill in the art. For example, a substantially pure population of bone marrow-derived MSCs can be achieved by growth of cells or by selection from a less pure population.

In some instances, the culture media comprising the therapeutic composition can be substantially free of any bone marrow-derived MSCs. A culture media that is substantially free of any bone marrow-derived MSCs can be about 75%, about 80%, about 85%, about 90% or more (e.g., 100%) free of any bone marrow-derived MSCs therein.

In other instances, the population of bone marrow-derived MSCs can include at least one MSC that is genetically modified.

In further instances, the population of bone marrow-derived MSCs can be autologous.

In one example, the therapeutic property endowed to the culture media (e.g., concentrated culture media) is the ability to promote recovery of urethral structure and function. In another example, the therapeutic property endowed to the culture media (e.g., concentrated culture media) is the ability to promote recovery of pudendal nerve structure and function. In a further example, the therapeutic property endowed to the culture media (e.g., concentrated culture media) is the ability to promote neovacularization, diminish inflammation, activate and/or cause differentiation of resident stem cells, or a combination thereof, at or about a target site.

The following examples are for the purpose of illustration only and are not intended to limit the scope of the claims, which are appended hereto.

Example 1

Methods

Age-matched virgin female Sprague-Dawley rats (225-250 g) were utilized in 3 experiments as approved by the Institutional Care and Animal Use Committee of the Cleveland Clinic.

To investigate if MSC home to pelvic organs after vaginal distension (VD), rats were randomized into 2 groups and underwent ex vivo whole organ fluorescence imaging (n=10) or immunofluorescence staining (n=8) one week after either VD (n=9) or sham VD (n=9) followed by intravenous (IV) infusion of green fluorescence protein labeled MSC (GFP+) 1 hour later. Three additional animals that did not receive cells were used as negative controls in each outcome.

To investigate if IV infused MSC accelerate recovery of continence after VD, rats were randomized into 3 groups: IV infusion of 2 million MSC in 1 ml saline via the lateral tail vein 1 hour after VD (VD+MSC; n=11); IV infusion of 1 ml saline via the lateral tail vein 1 hour after VD (VD+saline; n=12); or IV infusion of saline 1 hour after sham VD (sham VD+saline; n=11). Five animals in each group underwent histological assessment of the urethra 1 week after injury. The others underwent leak point pressure (LPP) and external urethral sphincter electromyography (EUS EMG) testing 1 week after injury.

To investigate if factors secreted by MSC accelerate functional recovery after VD, rats were randomized into 3 groups: periurethral injection of 300 µl concentrated conditioned media (CCM) 1 hour after VD (VD+CCM; n=10) via a low midline incision to expose the urethra; periurethral injection of 300 µl concentrated control media (CM) 1 hour after VD (VD+CM; n=9); or periurethral injection of CM 1 hour after sham VD (sham VD+CM; n=10). Five animals in each group underwent histological assessment of the urethra 1 week after injury. The others underwent LPP and EUS EMG testing 1 week after injury.

Stem Cell Harvest and Culture

Bone marrow from a donor female Sprague-Dawley rat was used to create cultured MSC as we have previously reported (Cruz, M A et al., *Obstet Gyne Intl*. Epub 2011 Sep. 21:2012). In brief, marrow was aspirated from the femur and tibia by flushing the bone and the cells were cultured in a normoxic incubator with 5% $CO_2$ at 37° C. At passage 3, cells were incubated and sorted for intracellular adhesion molecule I (ICAM-1) to select for MSC via flow cytometry. The MSC were transfected with pCCLsin.ppt.hPGK.GFP.pre, which uses a human PGK promoter to constitutively express GFP. After reaching confluence, cells were resorted and GFP-positive (GFP+) cells were collected. Cells were grown to passage 16 before being injected into rats, which was used to consistently ensure sufficient number of passages for thawing, sorting and transfection with our methods.

Preparation of Concentrated Conditioned Media (CCM)

CCM was obtained by incubating 100% confluent MSC in serum-free DMEM for 24 hours in a normoxic incubator with 5% $CO_2$ at 37° C. Cultured MSC supernatant was extracted and centrifuged at 4,000 rpm for 45 minutes (50× concentrated; 300 µl) and filtered with a sterile 0.22 µm filter. Conditioned media (CM) was created by processing serum-free DMEM that had not been utilized to culture cells though all the above steps. CCM was sampled and validated by a cell count and cell proliferation assays before being used. The validation tests showed no cells in the CCM and that MSC proliferated significantly faster in CCM than in CM.

MSC Characterization

To confirm expression of cell surface markers, MSC at P8 and P15 were stained and sorted using flow cytometry for CD29 (Cat102218 Biolegend), CD90 (Cat561404 BD), CD54 (Cat22389 Abcam), and CD45 (Cat559135 BD). To confirm the ability of MSC to differentiate into mesenchymal cell types, MSC at P16 were plated at a starting density of 50,000 cells/well and given regular MSC media, adipogenic differentiation media (A10070-01 Gibco), or osteogenic differentiation media (A10071-01 Gibco) every 3 days once confluent for 20-35 days. Cells in osteogenic media were fixed and stained with Alizarin Red S. Cells in adipogenic media were fixed and stained with Oil Red O and hematoxylin.

CCM Characterization

Content of CCM was assessed using the RAYBIO (RayBiotech, Inc. Norcross, Ga.) rat antibody protein array. CCM was desalted and incubated with array antibody support, biotinylated antibody and labeled with Streptavidin. Fluorescence was detected using a Xenogen IVIS 100 System which contains a supercooled charge-coupled camera in a light tight box. Relative concentration of each factor was quantified (Image J, NIH).

Vaginal Distension (VD)

VD was performed as previously described (Wood, H M et al., J Urology 180:753, 2008). The vagina was dilated under anesthesia by sequentially inserting increasing sized (24-32) Otis Bougie a Boule urethral dilators lubricated with surgilube. A modified 10 Fr Foley catheter was inserted into the vagina and the balloon was inflated to 3 ml for 4 hours. Sham VD consisted of vaginal accommodation and catheter insertion for 4 hours without balloon inflation.

Leak Point Pressure (LLP) and External Urethral Electromyography (EUS EMG) Recording LPP with simultaneous EUS EMG recording was done as previously described (Jiang, H H et al., Neurobiol Urodynamics 28:229, 2009) one week after injury. Rats were anesthetized with urethane (1.2 g/kg) i.p. and the urethra was exposed by opening the pubic symphysis with forceps. Bipolar parallel platinum electrodes (30-gauge needles 2 mm apart) were placed on the outside of the mid-urethra at the location of the EUS and connected to an amplifier (Model P511 AC Amplifier, Astro-Med, Inc.; band pass frequencies: 3 Hz-3 kHz) and electrophysiological recording system (DASH 8X, Astro-Med; 10 kHz sampling rate). A polyethylene catheter (PE-50) was inserted into the bladder via the urethra, and connected to both a pressure transducer (Astro-Med, Inc.) and syringe pump (KD Scientific). Bladder pressure was referenced to air pressure at the level of the bladder. Bladder pressure and EUS EMG were recorded while the bladder was filled with saline (5 ml/hr).

For LPP testing, an increase in intravesical pressure was made when the bladder was approximately half full by gradually pressing a cotton swab on the bladder until leakage occurred. At the moment of leakage, the cotton swab and the external pressure were rapidly removed. If a bladder contraction was induced by LPP testing, the results were not analyzed and the test was repeated. The test was repeated 6-8 times in each animal. Values of bladder pressure just prior to LPP testing (tonic activity) and at the peak pressure (peak value) of LPP testing were determined. Quantitative assessment of EUS EMG signals was performed by determining the mean rectified amplitude and the mean motor unit firing rate during tonic activity and at the pressure peak, as previously described (Jiang, H H et al., Neurobiol Urodynamics 28:229, 2009).

Ex Vivo Fluorescent Imaging

Seven days after VD or sham VD, rats were euthanized and the urinary bladder, urethra, vagina, rectum, lungs and spleen were harvested. Each organ was imaged using the Xenogen IVIS 100. Net total fluorescent flux (photons/second/cm$^2$/steridian) in a region of interest selected to include each organ was calculated by subtracting background flux from a negative control.

Immunofluorescent Staining

To investigate engraftment of MSC in the urethra and vagina, rats underwent intracardiac perfusion with heparinized saline followed by 4% formaldehyde one week after injury. The urethra and vagina were harvested en bloc and immersed in 20% sucrose. Tissues were cryosectioned (10 µm), fixed, and stained with a smooth muscle α-actin mouse monoclonal antibody (SC1306 Santa Cruz) followed by goat anti-mouse Texas red conjugated secondary antibody (SC2781 Santa Cruz). Slides were coverslipped with mounting medium containing DAPI. Sections were imaged on a confocal microscope.

Histology

To assess structural recovery of the urethra, it was harvested en block with the anterior vagina one week after injury and immersion fixed, paraffin embedded, sectioned, and stained with Masson's trichrome. EUS and urethral smooth muscle were graded independently on a semi-quantitative scale by 2 blinded investigators, with grade 1 representing significant disruption and grade 4 normal findings. Grade 4 EUS had contiguous muscle fibers, striations, and little extracellular matrix (ECM) infiltration. Grade 1 EUS demonstrated disruption of muscle fibers, no striations, and ECM infiltration. Grade 4 smooth muscle had large muscle bundles and little ECM infiltration. Grade 1 smooth muscle demonstrated very small muscle bundles and marked ECM infiltration. Grades 2 and 3 were scaled between 1 and 4. Elastin von Giesson stained slides were analyzed for presence or absence of elastin fibers.

Data Analysis

Mean values of each of the quantitative variables were calculated for each animal and were used to calculate a mean and standard error for each group. Wilcoxon Signed Rank test was used to compare control EMG data before and during LPP (Sigma Stat, Systat, Inc.). Student's t-test was used to compare quantitative variables in experiment 1. One-way ANOVA followed by a Holm-Sidak post hoc test was used to compare quantitative variables in experiments 2 and 3. $P<0.05$ indicated a statistically significant difference between groups. Quantitative data is presented as mean±standard error of the mean. Immunofluorescence was evaluated qualitatively by a blinded observer.

Results

Characterization and Differentiation of Bone Marrow Derived MSC

Figure 3A:
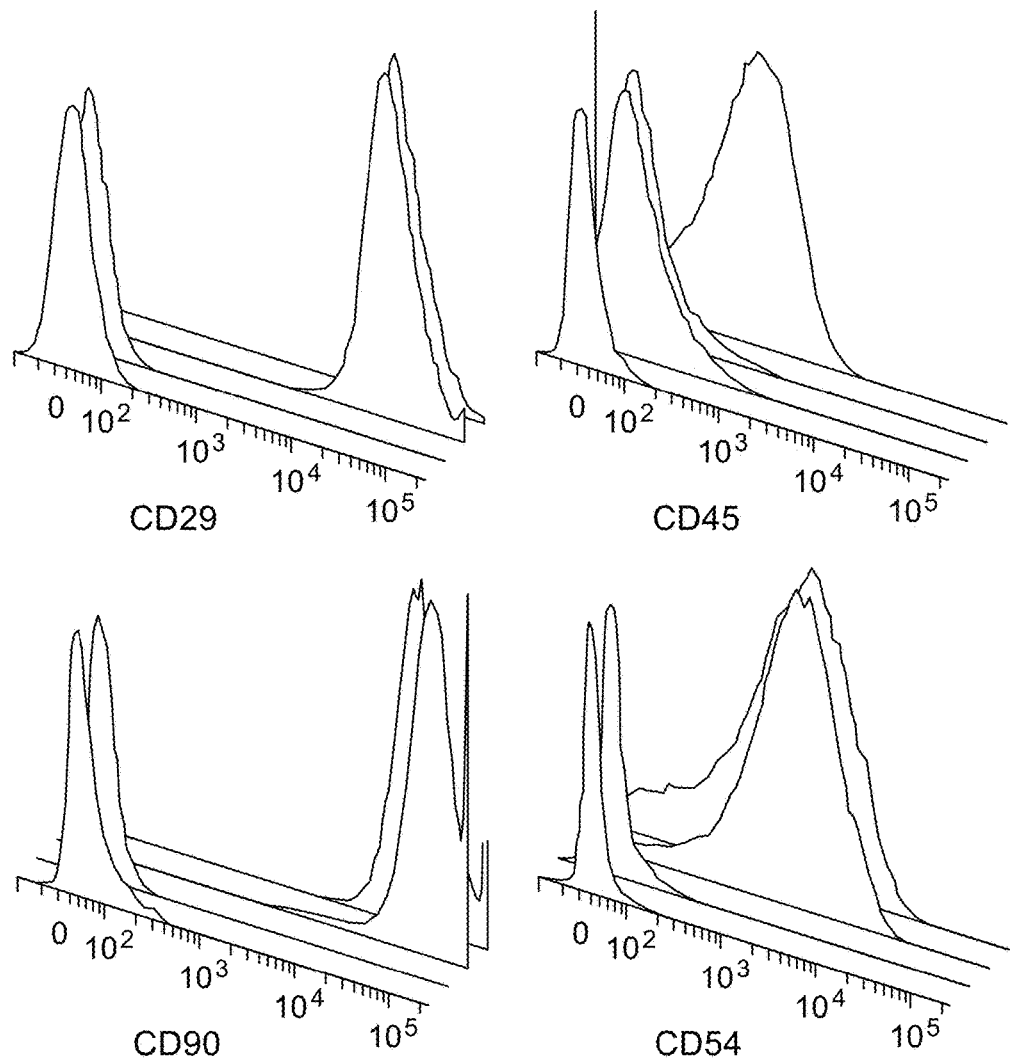
FIGS. 3A-B show the results of mesenchymal stem cell (MSC) characterization.
Figure 3B:
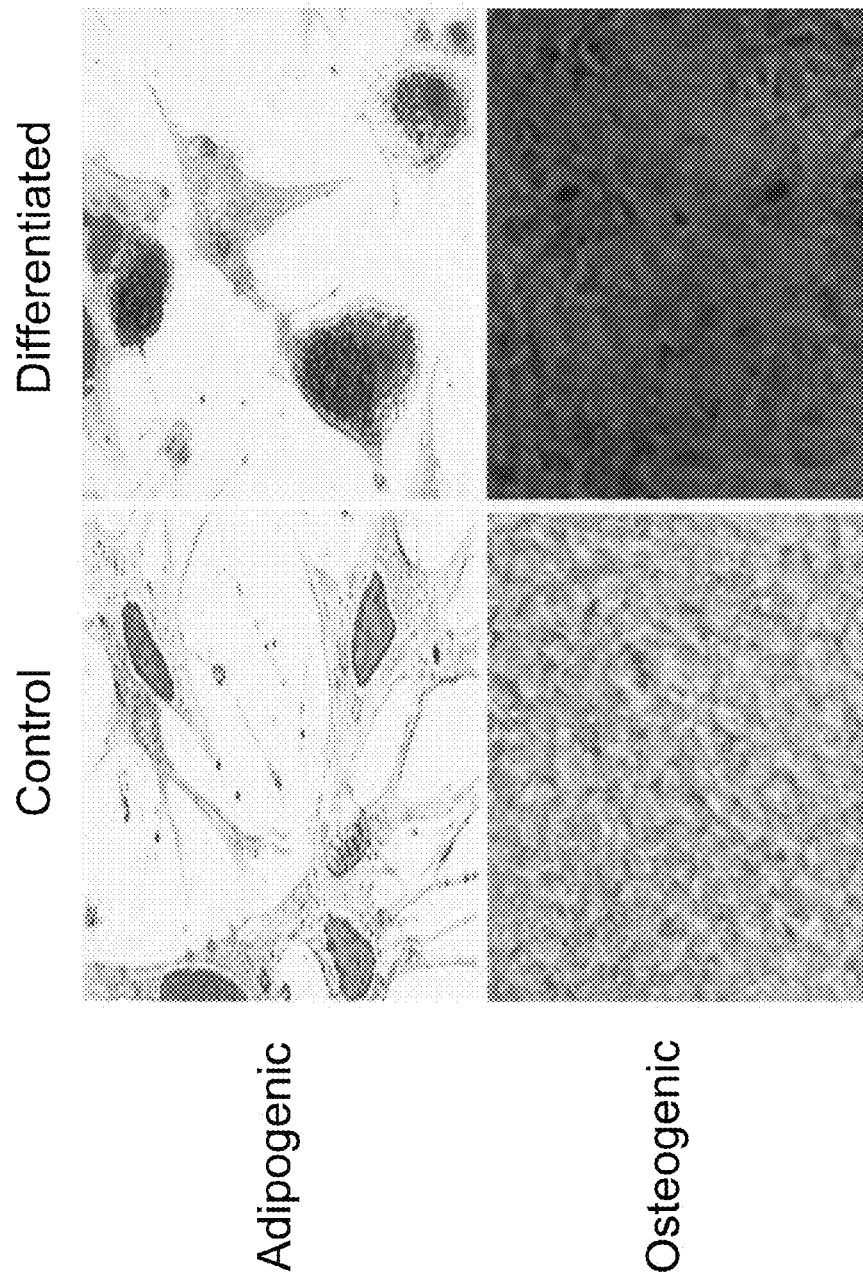

Our MSC expressed CD29, CD54 and CD90 but not CD45. Cells that were CD45−, CD29+, CD54+ and CD90+ accounted for 93.4% of our MSC population (FIGS. 3A-B). Adipogenic-induced cells contained intracellular lipid droplets, stained orange by oil red O (FIGS. 3A-B). Cells cultured under noninductive conditions did not accumulate lipid droplets. MSC cultured in osteogenic differentiation medium changed their spindle-shaped morphology to stellate and irregular shaped (FIGS. 3A-B). In control cultures, the cells preserved typical fibroblast morphology. These results demonstrate that the cells were predominately MSC with multi-lineage differentiation potential.

Characterization of MSC-Derived Factors in Conditioned Medium

CCM contained 63 cytokines (Table1).

TABLE 1

Antibody-based protein array analysis of rat bone marrow-derived MSC conditioned media under normoxic conditions analyzed with antibody-based array (+ to +++ indicate intensity of positive detection).

| Activin A | + | Integrin alpha M beta 2 | + |
|---|---|---|---|
| ADFP | + | Insulin | + |

TABLE 1-continued

Antibody-based protein array analysis of rat bone marrow-derived MSC conditioned media under normoxic conditions analyzed with antibody-based array (+ to +++ indicate intensity of positive detection).

| | | | |
|---|---|---|---|
| Adiponectin/Acrp30 | + | LIX | +++ |
| BDNF | + | L-Selectin/CD62L | +++ |
| beta-Catenin | + | MCP-1 | + |
| CD106 | + | MDC | + |
| CINC-2 alpha/beta | + | MIF | + |
| CINC-3 | + | MIP-1 alpha | + |
| CNTF | + | MIP-2 | +++ |
| CNTF R alpha | + | MIP-3 alpha | + |
| CSK | + | MMP-13 | + |
| CXCR4 | + | MMP-2 | + |
| IC-1 | ++ | MMP-8 | + |
| EG-VEGF/PK1 | + | MuSK | + |
| E-Selectin | + | Neuropilin-2 | + |
| Growth hormone | + | NGFR | + |
| Hepassocin | + | Orexin A | + |
| ICAM-1/CD54 | + | Osteopontin/SPP1 | + |
| ICK | + | RAGE | + |
| Insulin degrading enzyme | + | RALT/MIG-6 | + |
| IFN-gamma | + | Resistin | + |
| IL-1 alpha | + | TAL1A | + |
| IL-1 beta | + | TIE-2 | + |
| IL-1 R6/IL-1 R rp2 | + | TIMP-1 | + |
| IL-2 | + | TIM-2 | + |
| IL-3 | + | TLR4 | +++ |
| IL-4 | + | TRAIL | +++ |
| IL-5 | + | TROY | +++ |
| IL-6 | + | Ubiquitin | + |
| IL-10 | + | VEGF | + |
| IL-12/IL-23 p40 | + | VEGF-C | + |
| IL-13 | + | | |

MSC Homing of IV Infused MSCs

Figure 4A:
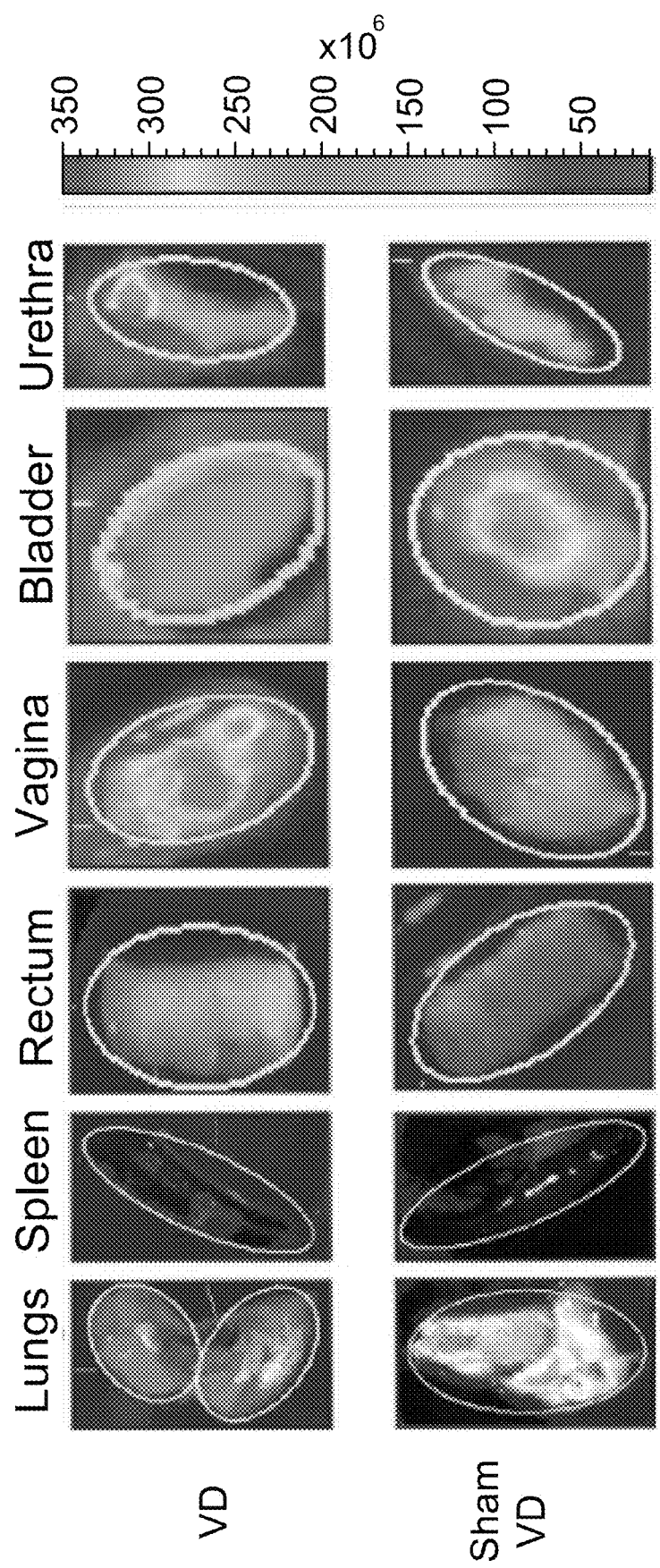
FIGS. 4A-C illustrate homing of MSCs to pelvic organs 1 week after vaginal distension (VD) and sham VD.
Figure 4B:
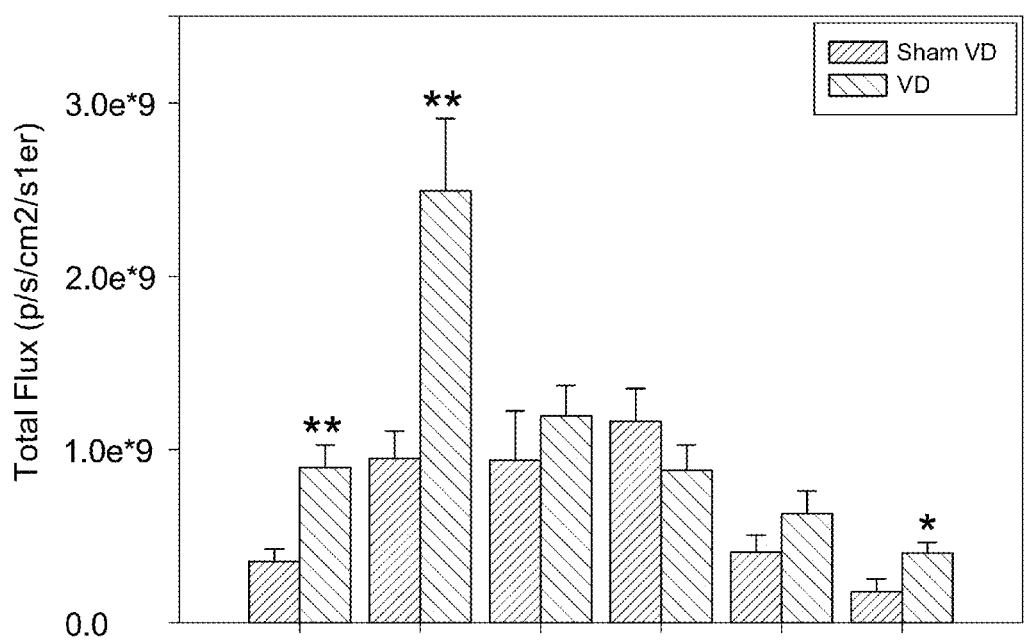
Figure 4C:
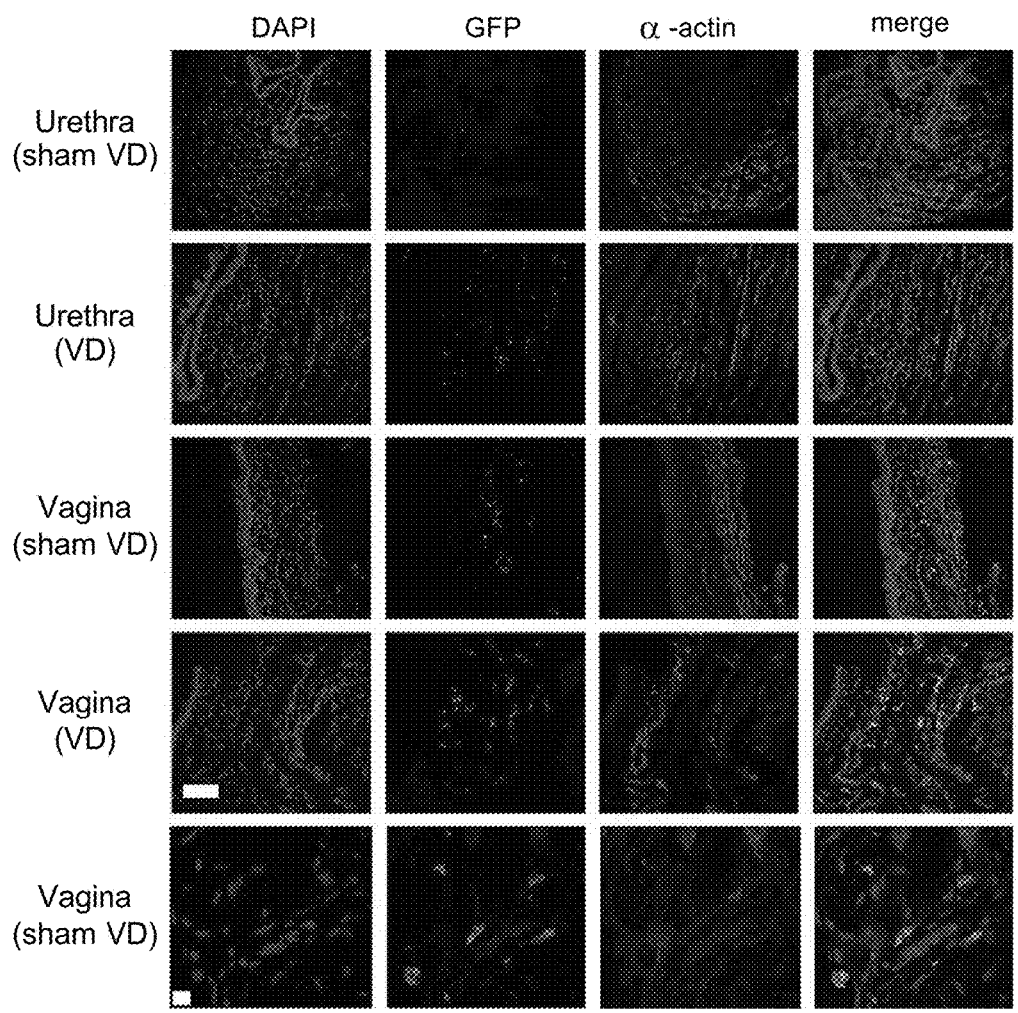
Figure 5A:
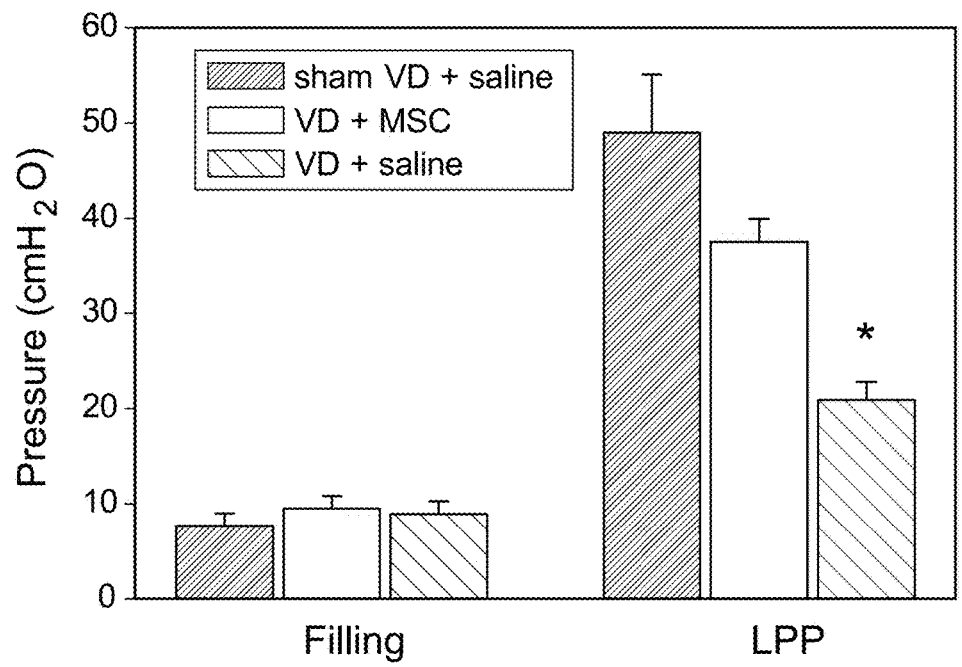
FIGS. 5A-F show the results of functional testing after vaginal VD or sham VD and treatment with MSC or saline (FIGS. 5A-C) or concentrated conditioned media (CCM) or control media (FIGS. 5D-F). Bladder pressure during filling and leak point pressure (LPP) testing (FIGS. 5A and 5D); external urethral sphincter electromyogram (EMG) firing rate during filling and LPP testing (FIGS. 5B and 5E); and external urethral sphincter EMG amplitude (FIGS. 5C and 5F). Each bar indicates mean±standard error of the mean of from 5-7 rats. * indicates a significant difference compared to the same outcome for the sham VD group with $p<0.05$.
Figure 5B:
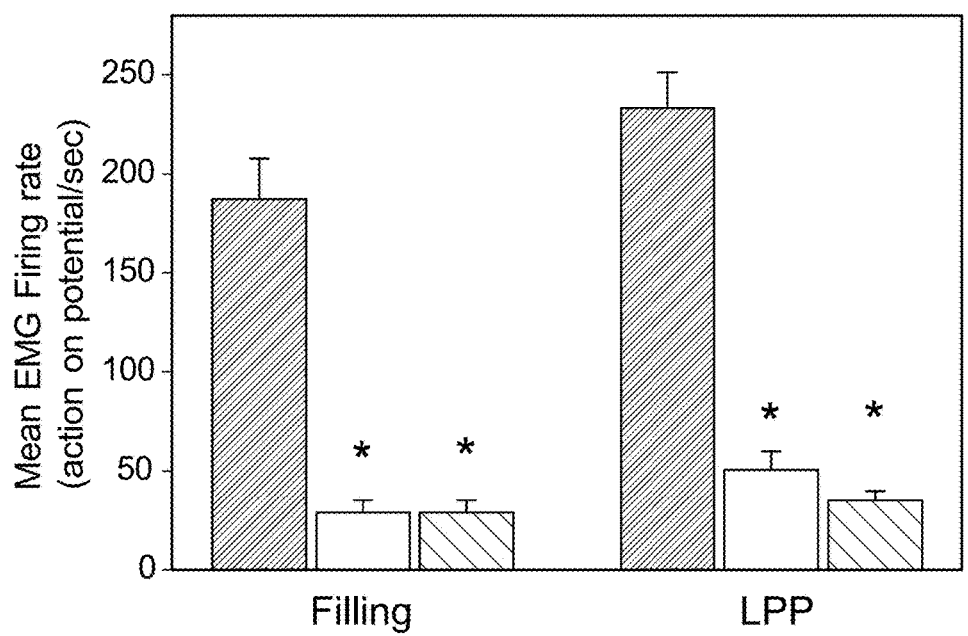
Figure 5C:
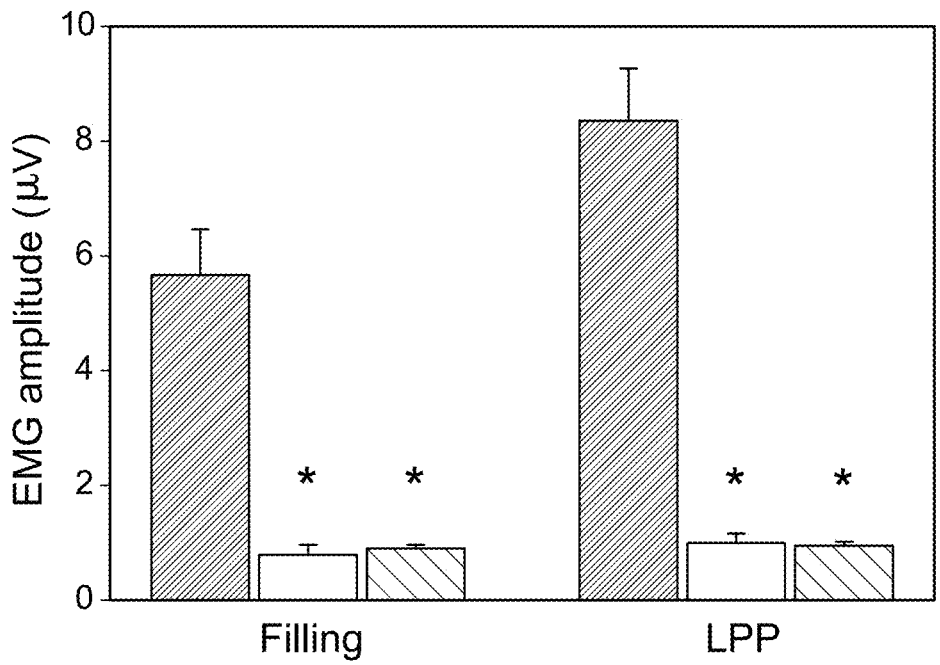
Figure 5D:
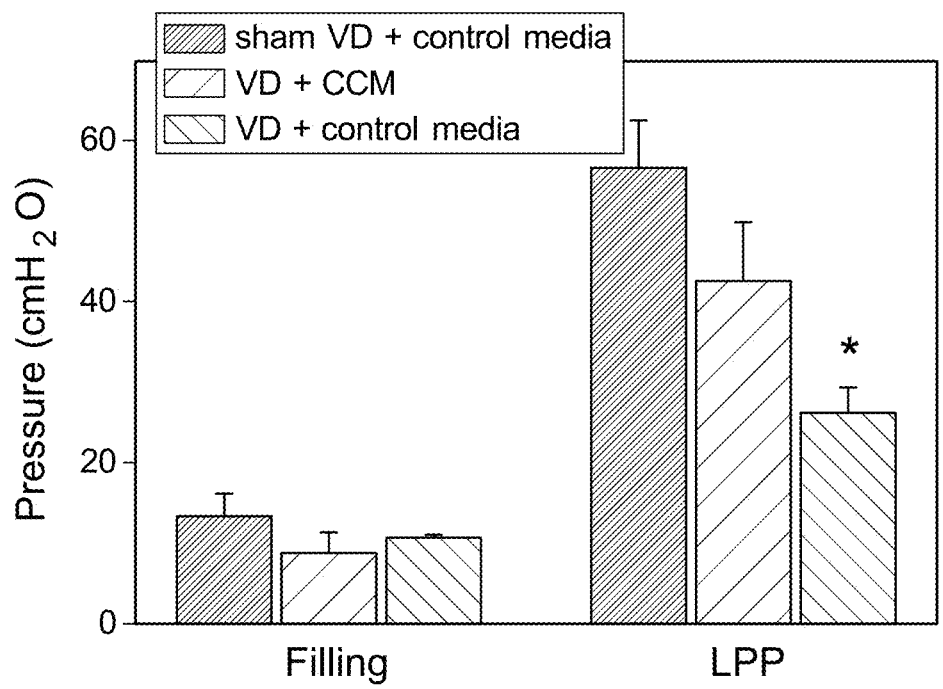
Figure 5E:
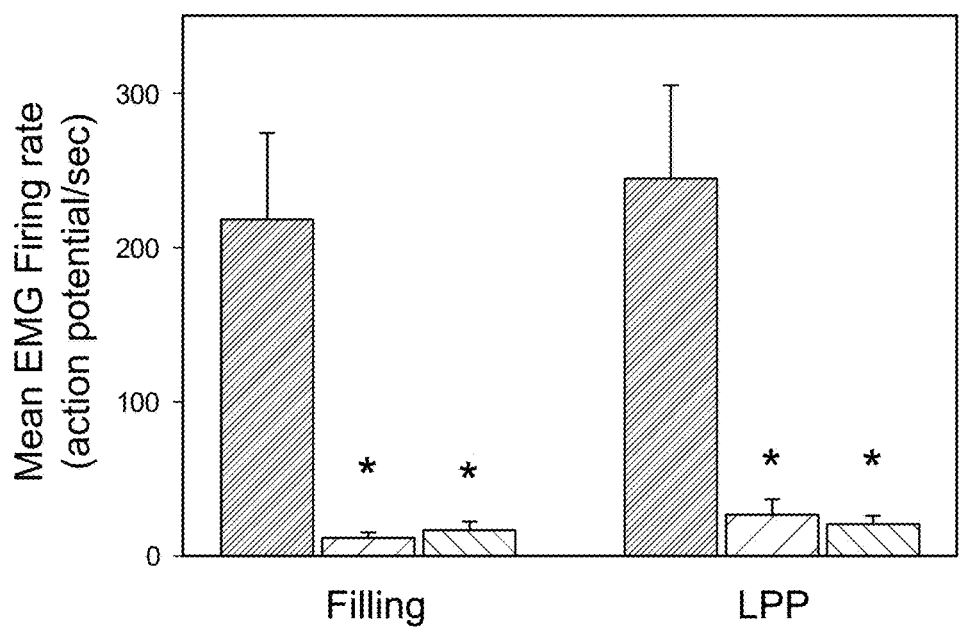
Figure 5F:
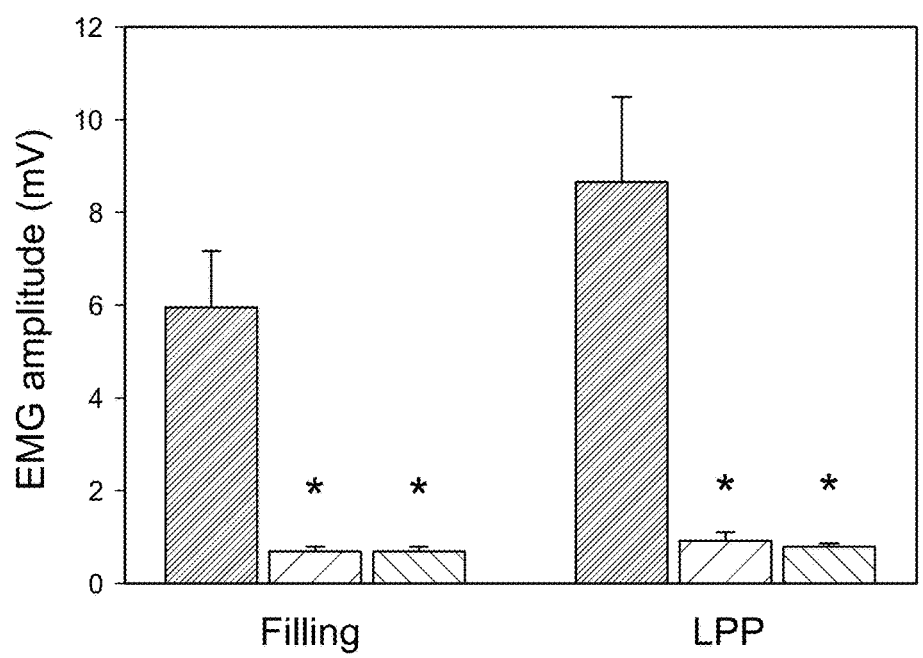
Figure 6A:
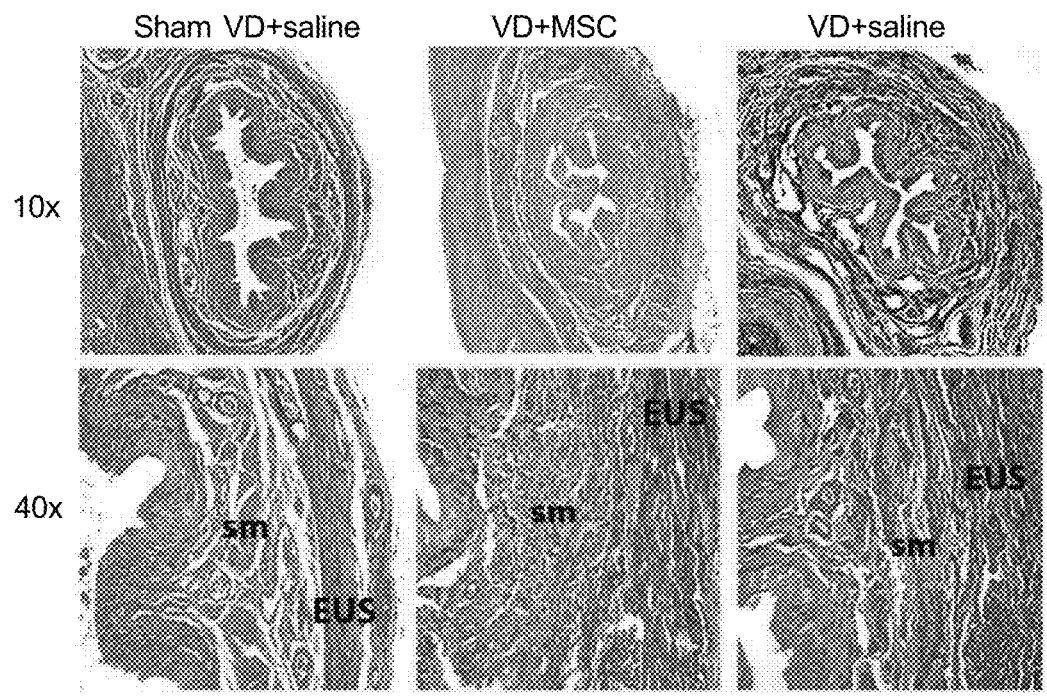
FIGS. 6A-D show urethral histology 1 week after VD or sham VD and treatment with MSC or saline (FIG. 6A) or CCM or control media (FIG. 6C). Results of semi-quantitative grading of urethral histology after VD or sham VD and treatment with MSC or saline (FIG. 6B) or CCM or control media (FIG. 6D). Each bar indicates mean±standard error of the mean from 5 rats. * indicates a significant difference compared to the same outcome for the sham VD group with $p<0.05$ (sm=smooth muscle; EUS=external urethral sphincter)
Figure 6B:
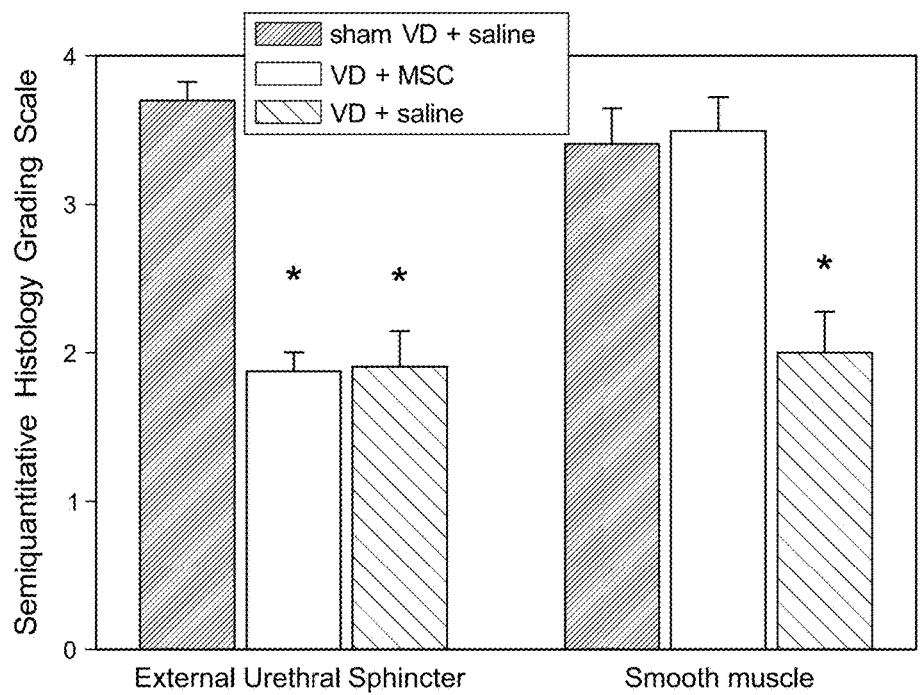
Figure 6C:
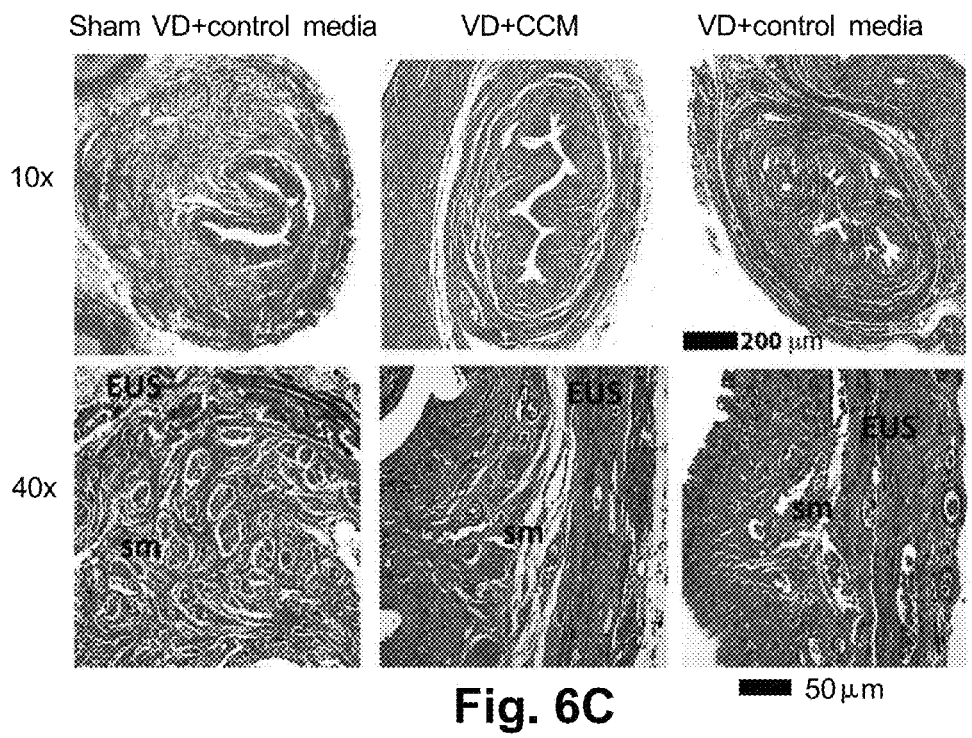
Figure 6D:
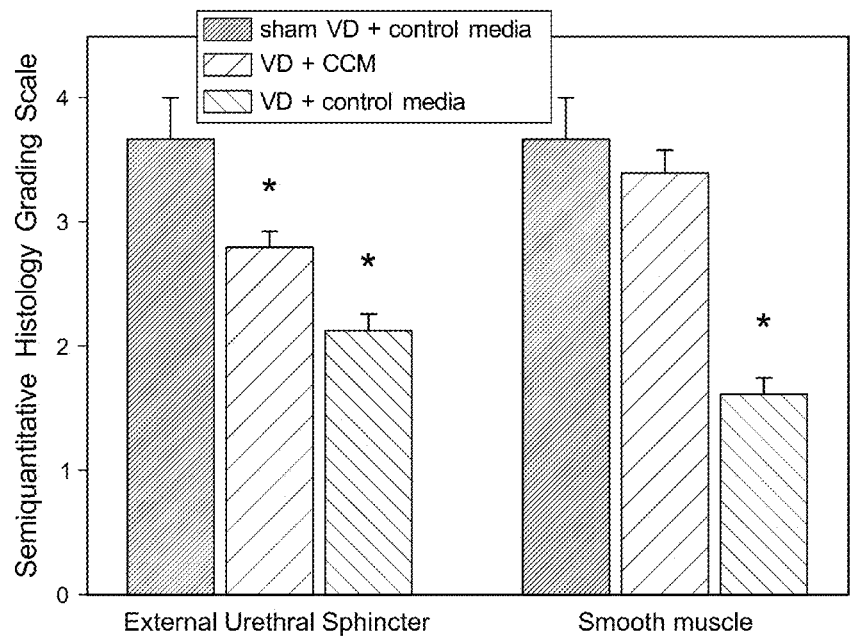

Urethra, vagina and spleen of rats that underwent VD had significantly higher mean total fluorescent flux than rats that underwent sham VD, indicating that MSC preferentially home to these organs after VD (FIGS. 4A-C). More GFP+ cells were evident in the smooth muscle of the urethra and vagina after VD than after sham VD, suggesting that IV infused MSC preferentially home to these smooth muscle layers (FIGS. 4A-C).

IV MSC and Local Injection of CCM Accelerate Functional Recovery

The VD+saline group demonstrated LPP and EUS EMG firing rates and amplitudes significantly lower than those after sham VD (FIGS. 5A-F). There was no significant difference in LPP between rats in the VD+MSC and sham VD groups, indicating that MSC facilitated urethral recovery. In contrast, EUS EMG firing rate and amplitude were significantly lower in the VD+MSC group than in the sham VD group, suggesting that MSC had not facilitated EUS recovery by 1 week after VD (FIGS. 5A-F).

LPP in the VD+CM group was significantly decreased compared to the sham VD group. LPP in the VD+CCM group was not significantly different from that of sham VD rats, indicating facilitation of urethral recovery by CCM. Similar to the results with MSC treatment, EUS EMG firing rate and amplitude were significantly decreased in all rats that received VD compared to rats that received sham VD, regardless of treatment, suggesting that CCM, like MSC, did not facilitate EUS recovery after VD at the 1 week time point (FIGS. 5A-F).

Effects of MSC and CCM on Urethral Structure

Sham VD rats had contiguous but thin EUS and urethral smooth muscle cells separated by ECM. VD caused disruption to urethral smooth and striated muscle as well as infiltration of ECM. The urethra of rats in the VD+MSC and VD+CCM groups appeared to have more complete smooth muscle layers than those in the VD+saline group (FIGS. 6A-D).

Urethral tissue from rats in the VD+MSC group were not significantly different in smooth muscle histology grade compared to sham VD rats but had a significantly higher smooth muscle histology grade than urethral tissue from the VD+saline group. Smooth muscle histology grade was not significantly different in the VD+CCM group compared to sham VD rats, while rats in the VD+CM group had significantly lower histology grades than sham VD rats (FIGS. 6A-D). Rats in the VD+MSC and VD+CCM groups had significantly lower EUS histology grade compared to sham VD rats, although the VD+CCM group had a higher score than the VD+MSC group. These results indicate that both MSC and CCM have positive effects on smooth muscle while MSC has no effect on EUS and CCM has only a mild effect on EUS (FIGS. 6A-D).

Figure 7B:
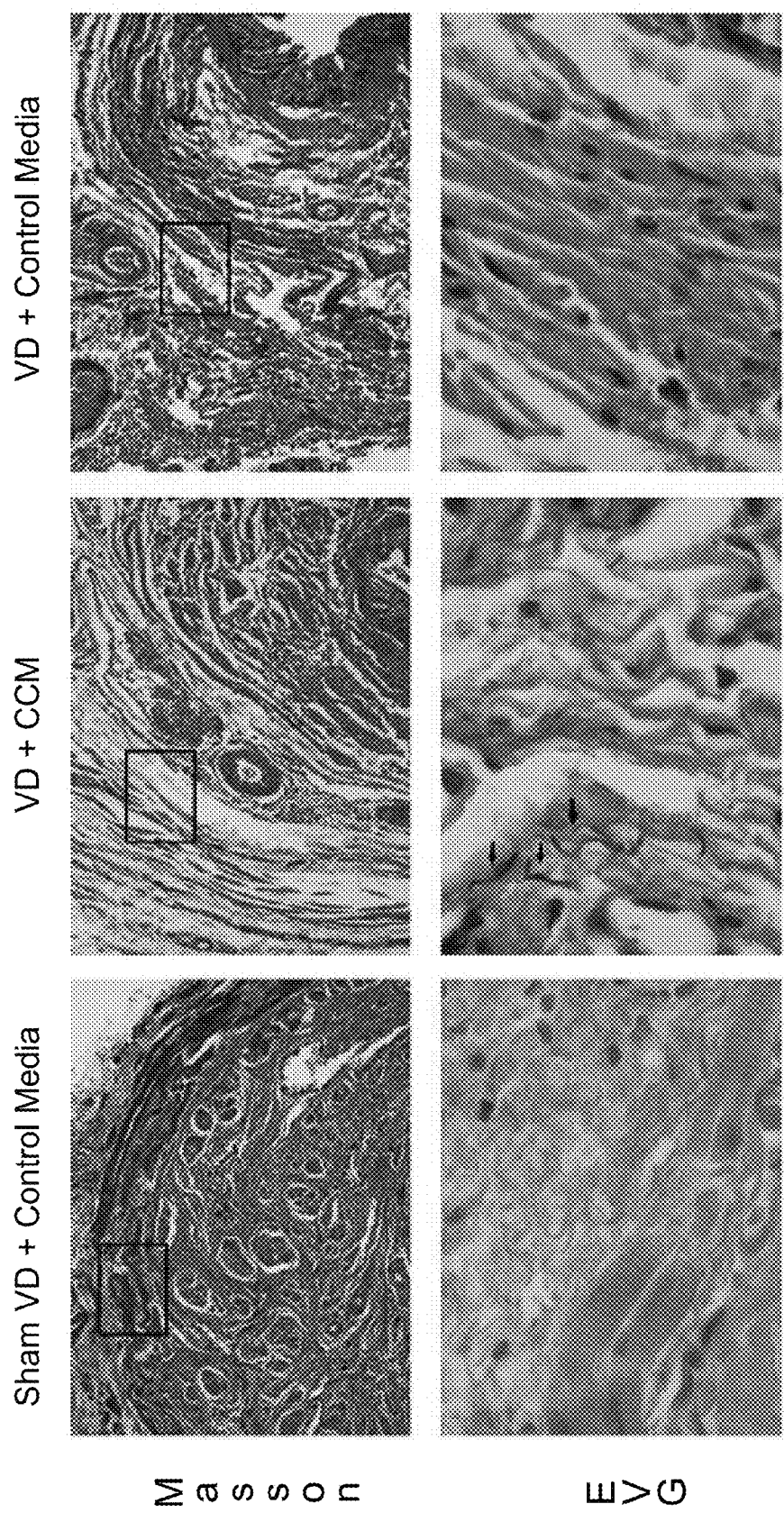

There were few to no elastin fibers in the urethra after sham VD or VD+saline. In contrast, aggregations of disorganized elastin fibers were identified near the EUS 1 week after VD+MSC (FIG. 7A-B). Similarly, VD+CM demonstrated little to no elastin but aggregations of disorganized elastin fibers were identified near the EUS 1 week after VD+CCM, suggesting that MSC facilitated production of elastin, likely by a paracrine effect on urethral smooth muscle cells and fibroblasts.

Example 2

Methods

The animal experiments were approved by the Louis Stokes Cleveland Department of Veterans Affairs Medical Center Institutional Animal Care and Use Committee and registered under the number 10-016-RT-003. Age-matched virgin female Sprague-Dawley rats (225-250 g) were randomized into 3 groups and underwent VD&PNC and were treated with 2 million green fluorescent protein (GFP)-labeled MSC IV (n=13), underwent VD&PNC and were treated with saline IV as a sham treatment 1 hour after injury (n=11), or underwent sham VD&PNC and received saline IV (n=12). Five of the animals in each group were euthanized 3 weeks after injury and treatment for qualitative histological assessment of the urethra. The remaining animals in each group underwent physiological testing 3 weeks after injury and treatment, including measurement of LPP, EUS electromyography (EMG), and pudendal nerve sensory branch potential (PNSBP).

Stem Cell Harvest and Culture

Bone marrow from a donor female Sprague-Dawley rat was used to create cultured MSC as previously reported (Cruz M A et al., *Obstetrics and Gynecology International* 2012; Epub 2011 Sep. 21). In brief, marrow was aspirated from the femur and tibia by flushing the bone with saline. Cells were cultured in a normoxic incubator with 5% $CO_2$ at 37° C. At passage 3, cells were incubated and sorted for intracellular adhesion molecule I (ICAM-1) to select for MSC via flow cytometry. The MSC were transfected with pCCLsin.ppt.hPGK.GFP.pre, which uses a human PGK promoter to constitutively express GFP. After reaching confluence, cells were resorted and GFP-positive (GFP+) cells were collected. Cells were grown to passage 16 before being injected into rats.

MSC Characterization

Expression of MSC cell surface markers were confirmed at P8 and P15 by sorting the cells with flow cytometry for CD29 (Cat102218 Biolegend), CD90 (Cat561404 BD), CD54 (Cat 22389 Abcam), and CD45 (Cat559135 BD). Differentiation of MSC into mesenchymal cell types was confirmed at P16 by plating the cells at a starting density of 50,000 cells/well in adipogenic differentiation media (A10070-01 Gibco) or osteogenic differentiation media (A10071-01 Gibco) every 3 days once confluent for 20-35 days. Cells in osteogenic media were fixed and stained with Alizarin Red S. Cells in adipogenic media were fixed and stained with Oil Red O and hematoxylin.

Vaginal Distention and Pudendal Nerve Crush (VD&PNC)

The pudendal nerves were accessed from a postero-lateral gluteal approach in anesthetized animals as we have done previously (Jiang H H et al., *Neurourology and Urodynamics* 2009; 28(3):229-35). The ilium and sacrum were opened slightly, and the pudendal nerve was isolated and crushed bilaterally with a Castroviejo needle holder twice for 30 sec. Sham PNC was performed by accessing the ischiorectal fossa with care not to stretch the nerve. Immediately after PNC or sham PNC, VD or sham VD were performed as previously described (Cruz M A et al., *Obstetrics and Gynecology International* 2012; Epub 2011 Sep. 21). In brief, the vagina was dilated under anesthesia by sequentially inserting increasing sized (24-32) Otis Bougie a Boule urethral dilators lubricated with surgilube. A modified 10Fr Foley catheter was inserted into the vagina and the balloon inflated to 3 ml for 4 hours. Sham VD consisted of vaginal accommodation with the urethral dilators and catheter insertion for 4 hours without balloon inflation.

Leak Point Pressure (LPP) with Simultaneous External Urethral Sphincter Electromyography (EUS EMG) Recording LPP was recorded simultaneous with EUS EMG as previously described 3 weeks after injury (Steward J E et al., *World Journal of Urology* 2010; 28:365-71). In brief, rats were anesthetized with urethane (1.2 g/kg) i.p. and the urethra exposed by opening the pubic symphysis with micro-dissection scissors. Bipolar parallel platinum electrodes (30-gauge needles 2 mm apart) were placed on the outside of the mid-urethra at the location of the EUS and connected to an amplifier (Model P511 AC Amplifier, Astro-Med, Inc., Providence, R.I.; band pass filtering: 3-3 kHz) and electrophysiological recording system (Powerlab 8/35 & LabChart 7, ADInstruments, Colorado Springs, Colo.; 10 kHz sampling rate). A polyethylene catheter (PE-50) was inserted into the bladder dome, and connected to both a pressure transducer (model PT300, Grass Telefactor, West WarwickRI) and syringe pump (KD Scientific). Bladder pressure was referenced to air pressure at the level of the bladder. Bladder pressure and EUS EMG were recorded while the bladder was filled with saline (5 ml/hr).

For LPP testing, intravesical pressure was increased when the bladder was approximately half full (0.3 ml) by gradually applying pressure with a cotton swab until leakage occurred. At the moment of leakage, the cotton swab and the external pressure were rapidly removed. If a bladder contraction was induced by LPP testing, the results were not analyzed and the test was repeated. The test was repeated 6-8 times in each animal. Values of bladder pressure just prior to LPP testing (tonic activity) and at the peak pressure (peak value) of LPP testing were determined. Quantitative assessment of EUS EMG signals was performed by determining the mean rectified amplitude and the mean motor unit firing rate during tonic activity and at the pressure peak, as previously described (Cruz Y et al., *Advances in Applied Electromyograms*. Rijeka, Croatia: Intech Publishing; 2011, pp. 189-212). Data analysis was performed using LabChart 7 with a detection threshold of 15 μV and peaks threshold of 15 μV.

Pudendal Nerve Sensory Branch Potential (PNSBP) Recording

For PNSBP recordings, the pubis and ischium were partly removed using forceps to separate and enlarge the ischiorectal fossa where Alcock's canal is located. The sensory branch of the pudendal nerve was identified in Alcock's canal and separated from the two motor branches and the pudendal artery using a dissecting needle under a surgical microscope. The sensory branch was guided over bipolar parallel platinum electrodes identical to those used to record EUS EMG and both were placed in a warm (37° C.) mineral oil bath. As above, the electrodes were connected to an amplifier (Model P511 AC Amplifier, Astro-Med, Inc., Providence, R.I.; band pass frequencies: 3 Hz-3 kHz) and the electrophysiological recording system (PowerLab 8/35; 10 kHz sampling rate). Following baseline PNSBP recordings, the clitoris was lightly brushed to measure the response of the sensory branch to sensory stimulation.

Histology

To assess structural recovery of the urethra, it was harvested en block with the anterior vagina 3 weeks after injury and immersion fixed, paraffin embedded, transversely sectioned (5 μm), and stained with Masson's trichrome and elastin von Giesson stains. Masson's trichrome was utilized to qualitatively assess the EUS. Elastin von Giesson stained slides were analyzed for presence or absence of elastin fibers.

Data Analysis

Mean values of each of the quantitative variables were calculated for each animal and were used to calculate a mean and standard error of the mean (sem) for each group. Results are presented as mean±standard error of the mean of each group. Quantitative data was statistically analyzed with a one-way ANOVA followed by a Student-Newman-Keuls test, with $p<0.05$ indicating a significant difference between groups (Sigma Stat, Systat, Inc.). Histology results were evaluated qualitatively by a blinded observer.

Results

Figure 8A:
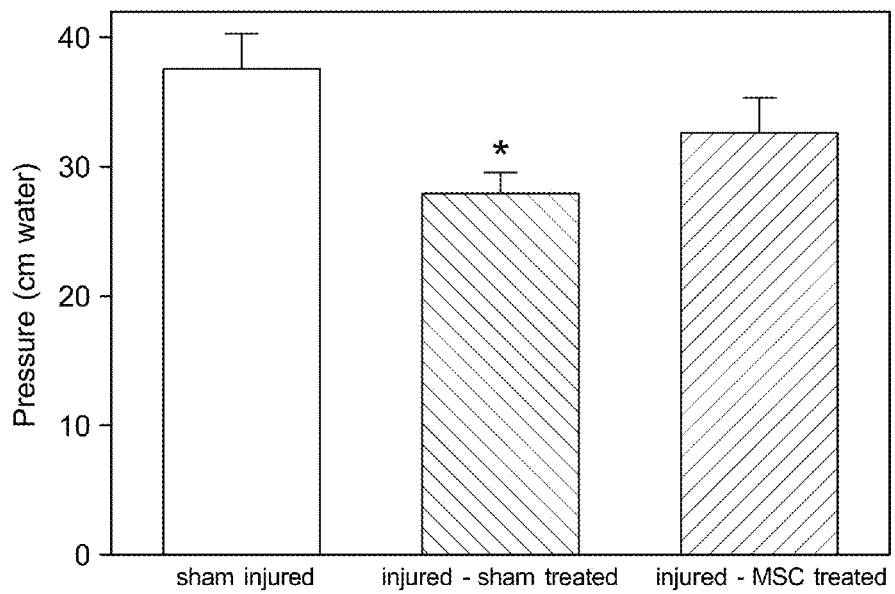
FIGS. 8A-C show the results of functional continence testing 3 weeks after vaginal distension and pudendal nerve crush (VD&PNC) or sham VD&PNC and treatment with MSCs or saline.
Figure 8B:
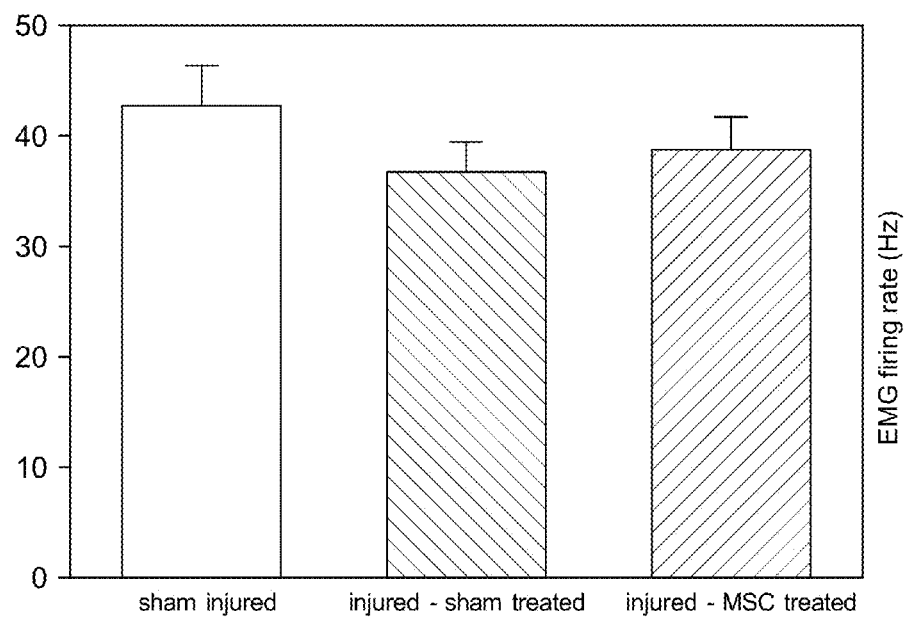
Figure 8C:
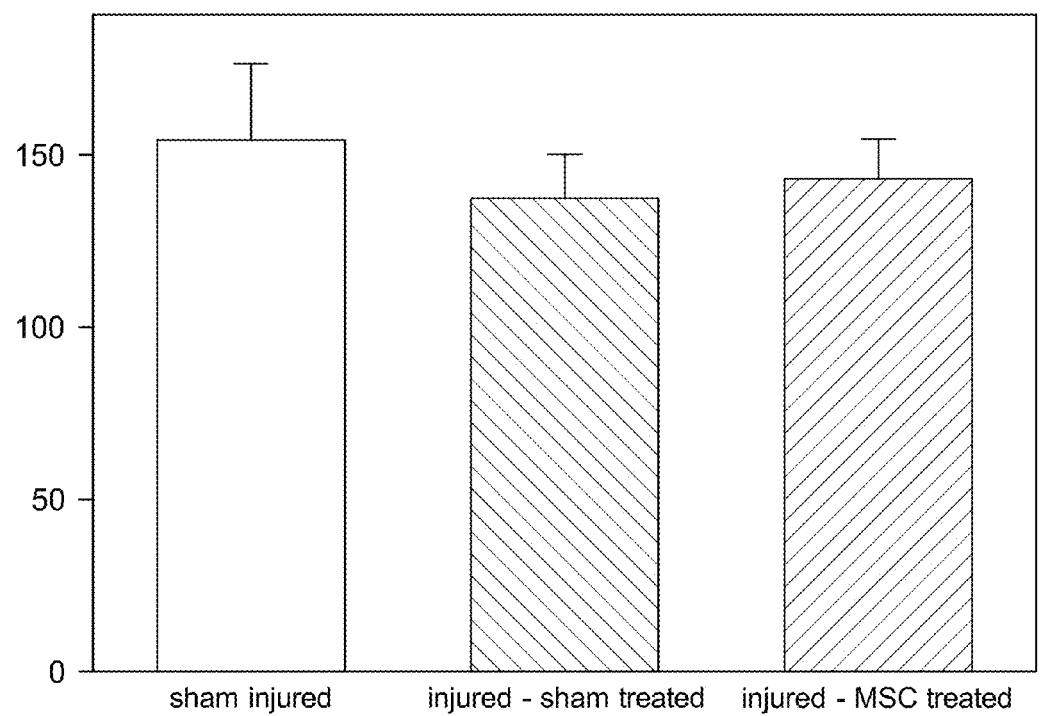
Figure 9A:
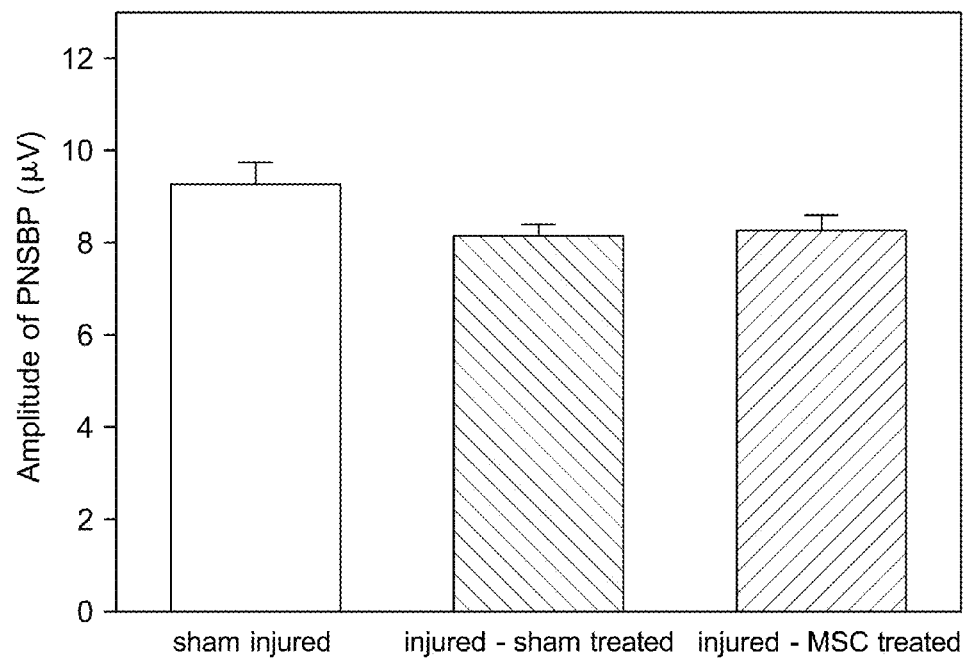
FIGS. 9A-F show the Results of neurological functional testing 3 weeks after vaginal distension and pudendal nerve crush (VD&PNC) or sham VD&PNC and treatment amplitude rate during the clitoral brushing test showing amplitude of pudendal nerve sensory branch potential (PNSBP) at baseline.
Figure 9B:
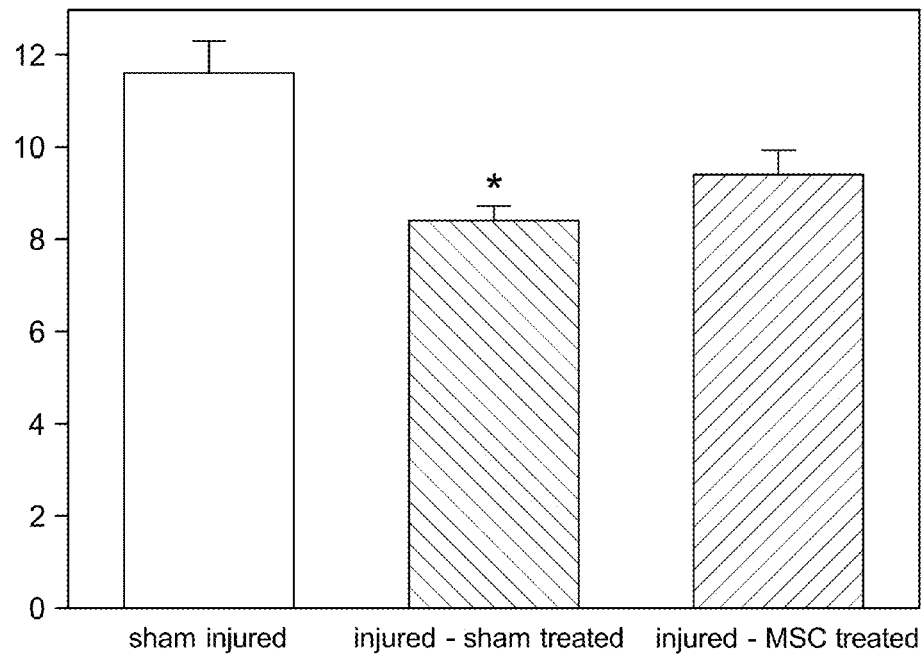
Figure 9C:
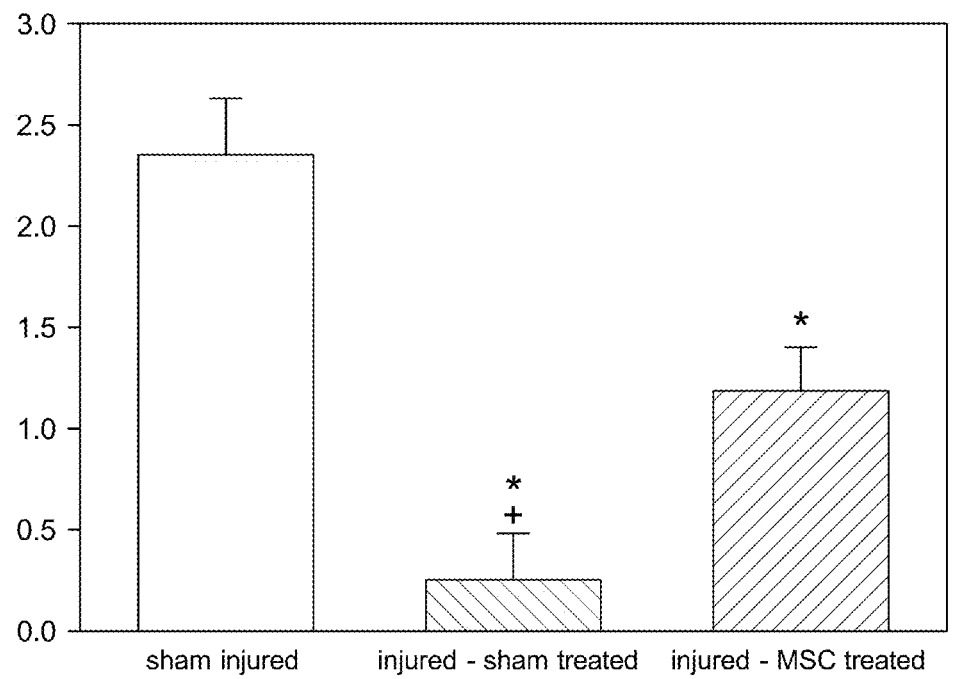
Figure 9D:
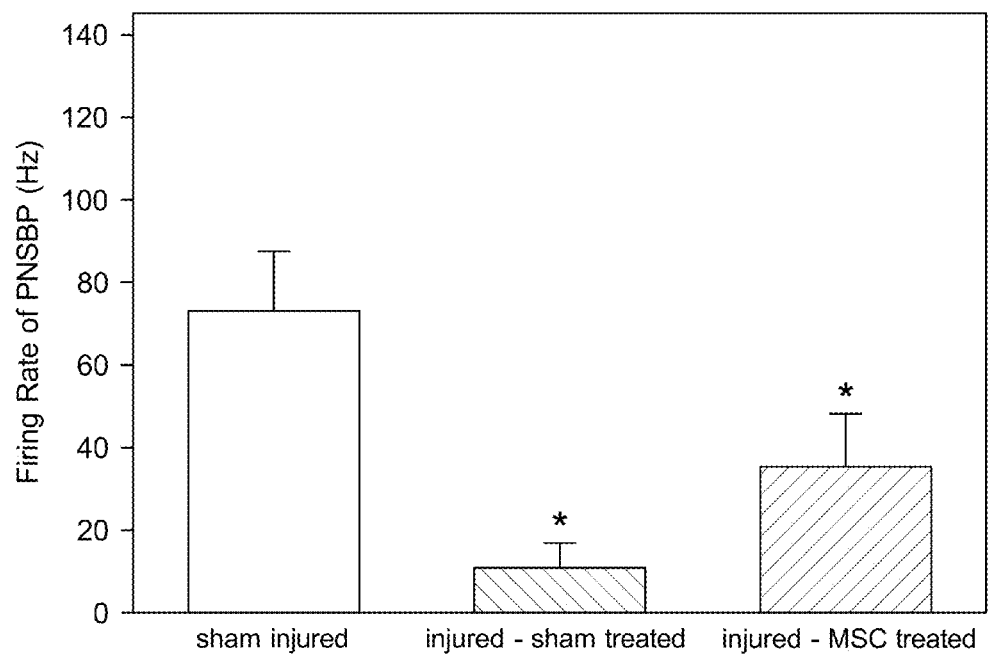
Figure 9E:
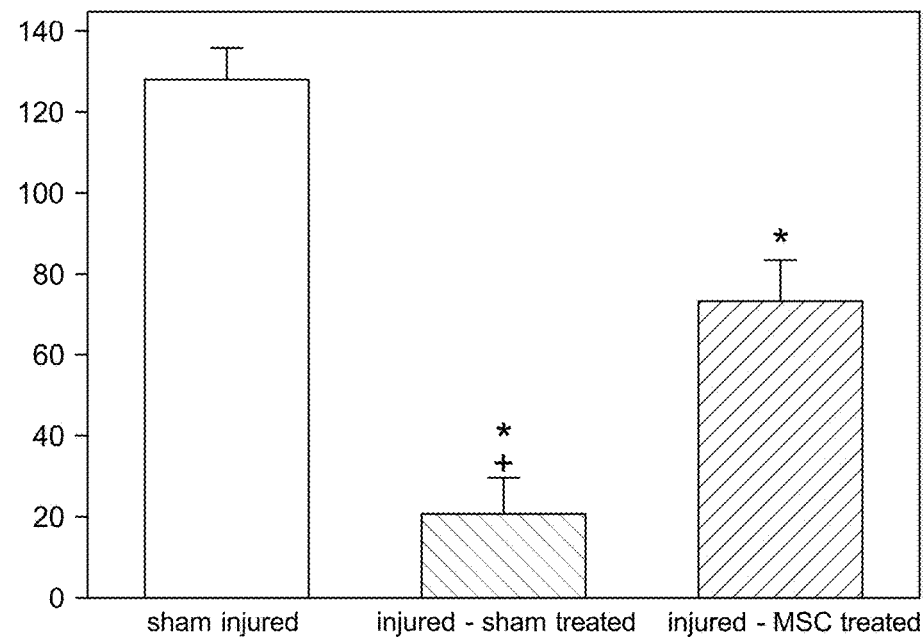
Figure 9F:
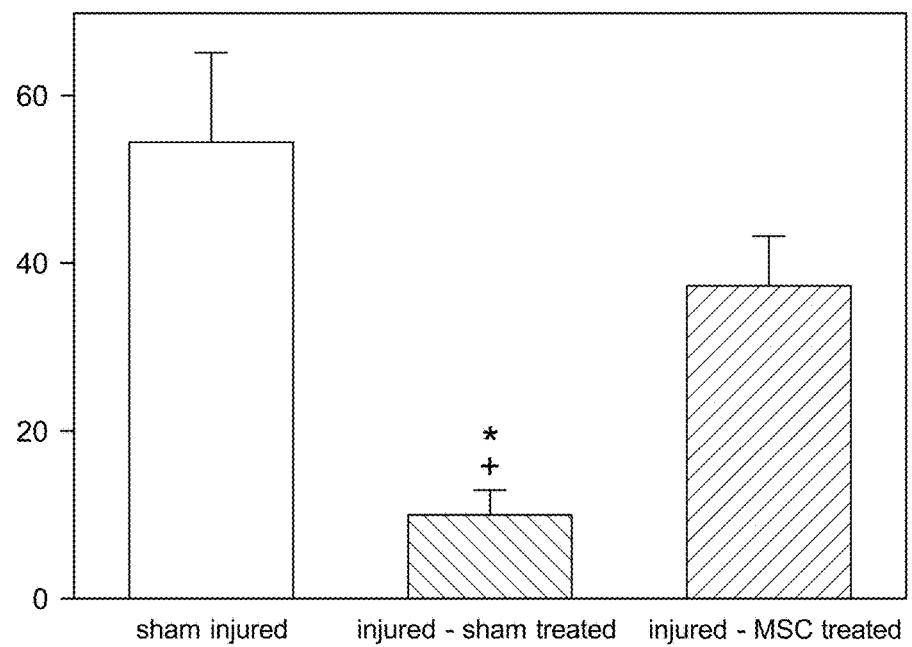

Peak pressure during LPP was significantly reduced 3 weeks after VD&PNC with saline treatment compared to sham injured animals, indicative of SUI, as we have observed previously (Jiang H H et al., *Neurourology and Urodynamics* 2009; 28(3):229-35). In contrast, LPP in rats that received IV MSC after VD&PNC was not significantly different from either of the other groups, suggesting that treatment with MSC maintained partial continence function after this simulated childbirth injury (FIGS. 8A-C). EUS EMG amplitude and frequency at baseline and during LPP were not significantly different between the 3 groups (FIGS. 8A-C).

There was no significant difference between the 3 groups in amplitude of PNSBP at baseline (FIGS. 9A-F). However, during clitoral brushing, amplitude of PNSBP 3 weeks after sham injury was significantly greater than 3 weeks after VD&PNC treated with saline but not after VD&PNC treated with MSCs, suggesting incomplete pudendal nerve recovery 3 weeks after injury with MSC treatment. When baseline PNSBP amplitude was subtracted from peak PNSBP amplitude to obtain a measure of the response of the pudendal nerve sensory branch to a stimulus (clitoral brushing), saline-treated VD&PNC rats responded significantly less than either sham-injured or MSC-treated VD&PNC rats, while sham-injured rats responded significantly more than MSC-treated VD&PNC rats. This indicates that, despite evidence of incomplete pudendal nerve recovery, MSC treatment maintained partial neurological function 3 weeks after VD&PNC (FIGS. 9A-F).

The results of amplitude of PNSBP were paralleled in firing rate of the pudendal nerve sensory branch, although the outcomes were not identical. Firing rate of PNSBP at baseline was significantly decreased in both VD&PNC groups regardless of treatment compared to the sham-injured group, suggesting incomplete neural recovery after injury, even with MSC treatment (FIGS. 9A-F). Peak firing rate of PNSBP was significantly decreased in saline-treated VD&PNC rats compared to both sham-injured rats and MSC-treated VD&PNC rats. There was also a significant difference in peak firing rate between MSC-treated VD&PNC rats and sham-injured rats suggesting that MSC treatment maintained only partial neurological function 3 weeks after injury. When baseline PNSBP firing rate was subtracted from peak PNSBP firing rate to obtain a measure of the response of the pudendal nerve sensory branch to a stimulus, saline-treated VD&PNC rats responded significantly less than either sham-injured or MSC-treated VD&PNC rats, suggesting a significant effect of MSC on maintenance of neural function after injury (FIGS. 9A-F).

Masson's trichrome stained urethras demonstrated a healthy EUS with closely opposed, long striated muscle fibers that maintained full integrity, as previously demonstrated (Pan H Q et al., *American Journal of Physiology-Renal Physiology* 2009; 296:277-83). Three weeks after VD&PNC and saline treatment, there were few striated muscle fibers in the EUS (FIGS. 10A-C). Those that were present were highly disrupted by connective tissue infiltration, as previously observed after this simulated childbirth injury in the absence of treatment (Pan H Q et al., *American Journal of Physiology-Renal Physiology* 2009; 296:277-83). Three weeks after VD&PNC and IV MSC treatment, the EUS demonstrated few striated muscle fibers, but more than with saline treatment, and less connective tissue infiltration than with saline treatment, suggesting that MSC treatment lead to partial recovery of anatomy after this simulated childbirth injury. No elastin was noted on elastin von Giesson stained urethras from animals in any of the experimental groups.

Example 3

Methods

Age-matched virgin female Sprague-Dawley rats were utilized in 3 experiments. The first functional study, utilizing MSCs, had 3 groups: pudendal nerve crush (PNC) receiving IV phosphate buffered saline (PBS; N=6); PNC receiving 2 million GFP-labeled MSCs IV (N=6); and sham PNC receiving IV saline (N=6). The second functional study, utilizing media that had been conditioned by MSCs and then concentrated (CCM), had 3 groups: PNC receiving CCM by local injection to the crush site of the pudendal nerve (N=6); PNC receiving a local control media injection (N=6); and sham PNC receiving a local control media injection (N=6). The third homing study had 2 groups: PNC receiving IV MSCs (N=11); and sham PNC receiving IV MSCs (N=11).

PNC was performed by crushing the pudendal nerve in the ischiorectal fossa using a Castroveijo needle holder 2 consecutive times, 30 seconds each time. One hour after PNC, 2 million MSCs or PBS were injected via the tail vein. Conditioned MSCs or control media were concentrated 50 times and injected directly into the crushed site 1 hour after injury. LPP and external urethral sphincter (EUS) EMG were tested 10 days after treatment. The pudendal nerve, urethra, vagina, bladder, rectum, and spleen were harvested and imaged ex vivo for GFP 2, 4, and 10 days after injection.

Results

Figure 11A:
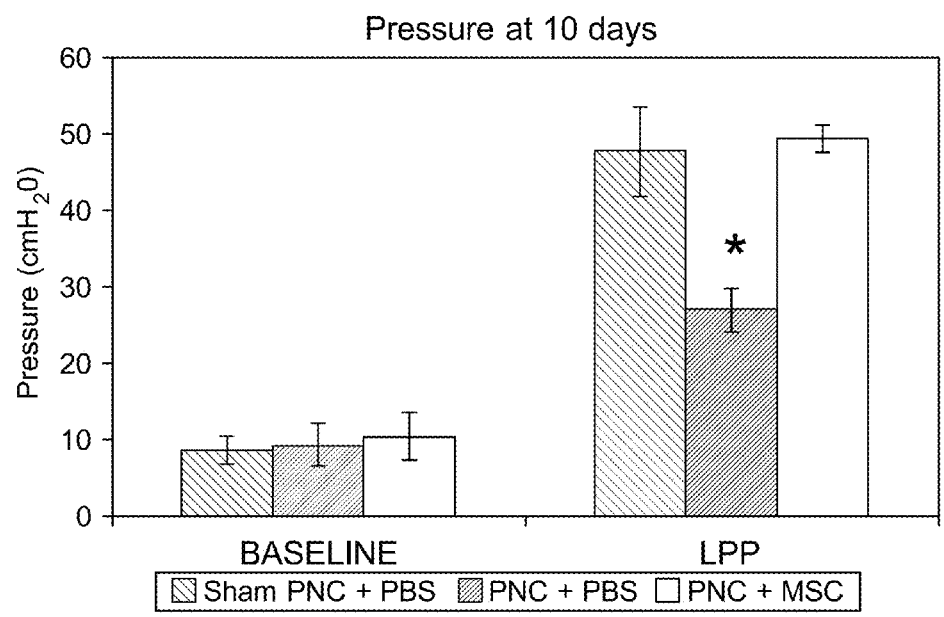
FIGS. 11A-B are a series of histograms showing that LPP was significantly reduced in PNC rats treated with PBS or control media compared to sham PNC, but not in those given IV MSCs or CCM.
Figure 11B:
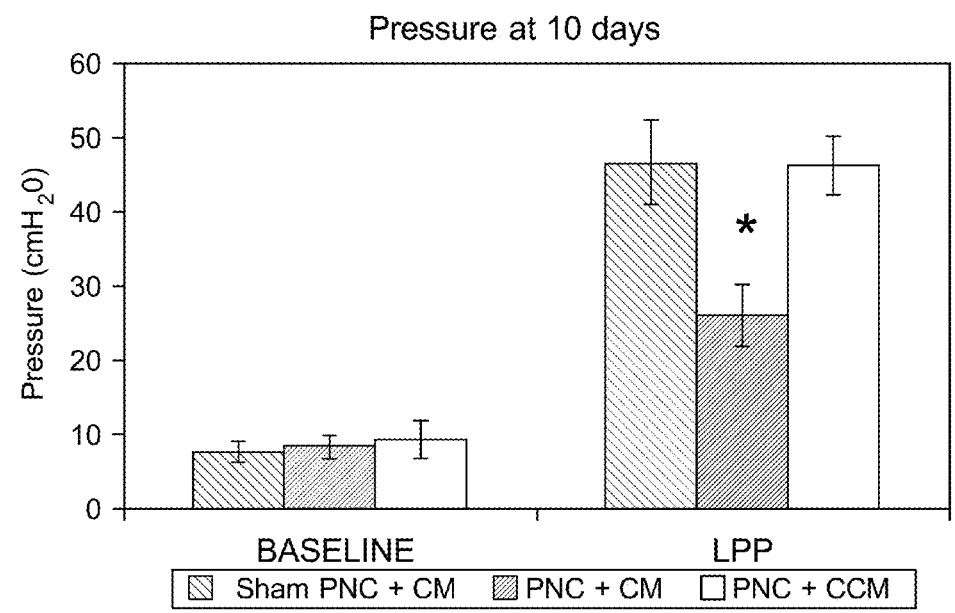
Figure 12A:
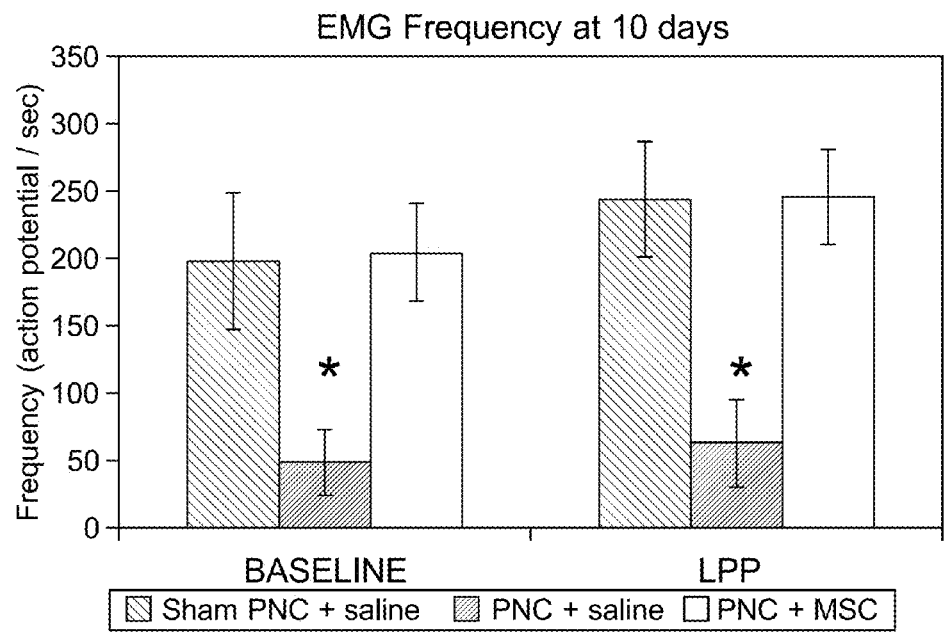
FIGS. 12A-B are a series of histograms showing EUS EMG frequency both at baseline and during LPP were significantly decreased in PNC rats treated with PBS or control media compared to sham PNC, but not in those given IV MSCs or CCM.
Figure 12B:
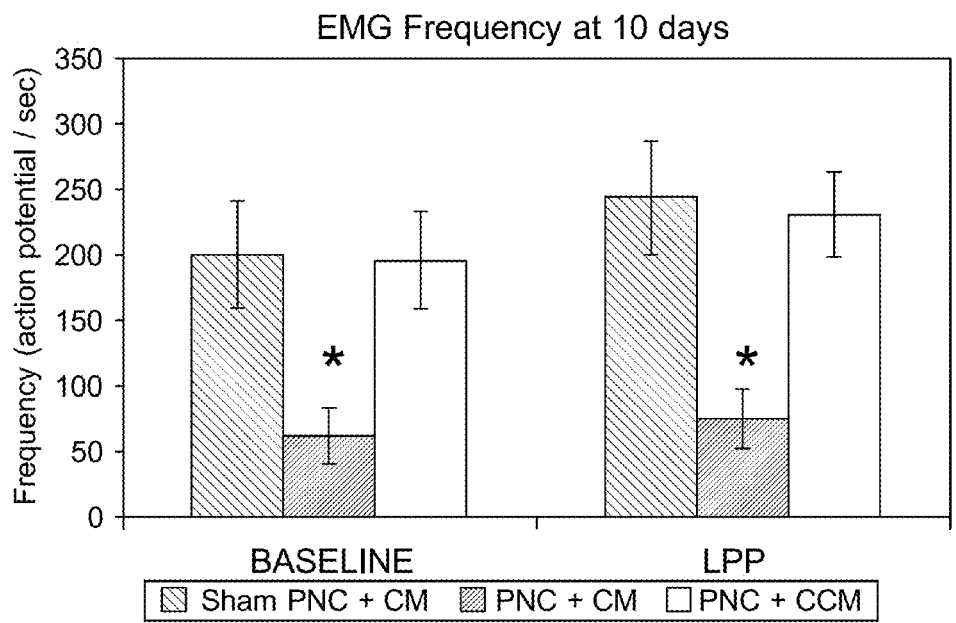
Figure 13A:
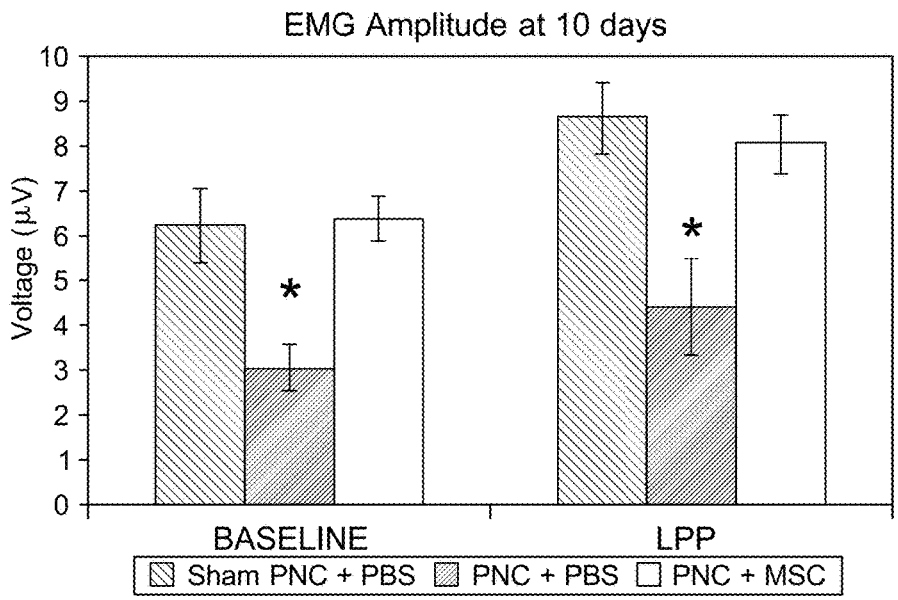
FIGS. 13A-B are a series of histograms showing EUS EMG amplitude both at baseline and during LPP were significantly decreased in PNC rats treated with PBS or control media compared to sham PNC, but not in those given IV MSCs or CCM.
Figure 13B:
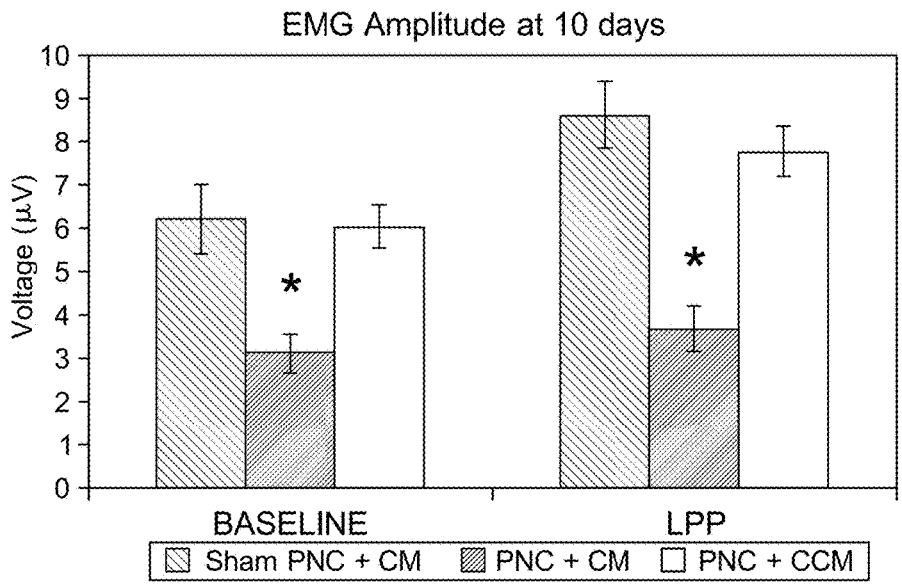
Figure 14A:
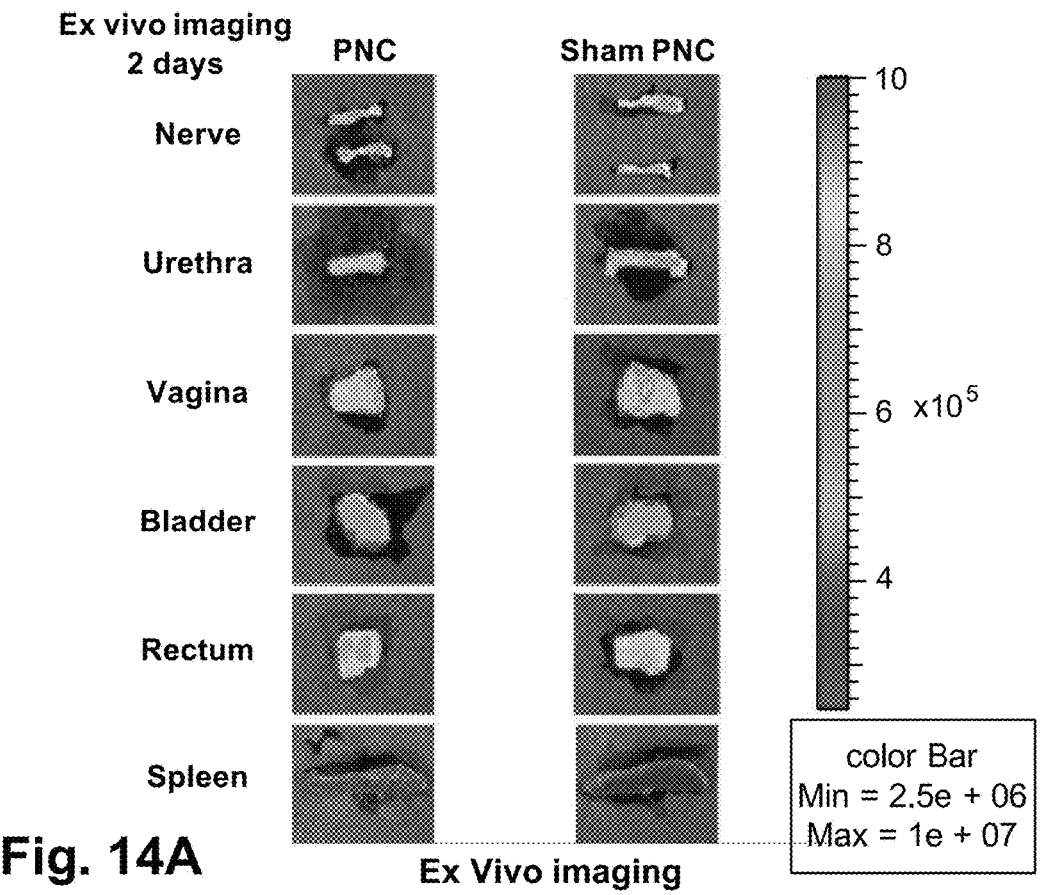
FIGS. 14A-B show the results of ex vivo imaging indicating significantly increased fluorescence in the pudendal nerve and spleen of PNC rats receiving IV MSC.
Figure 14B:
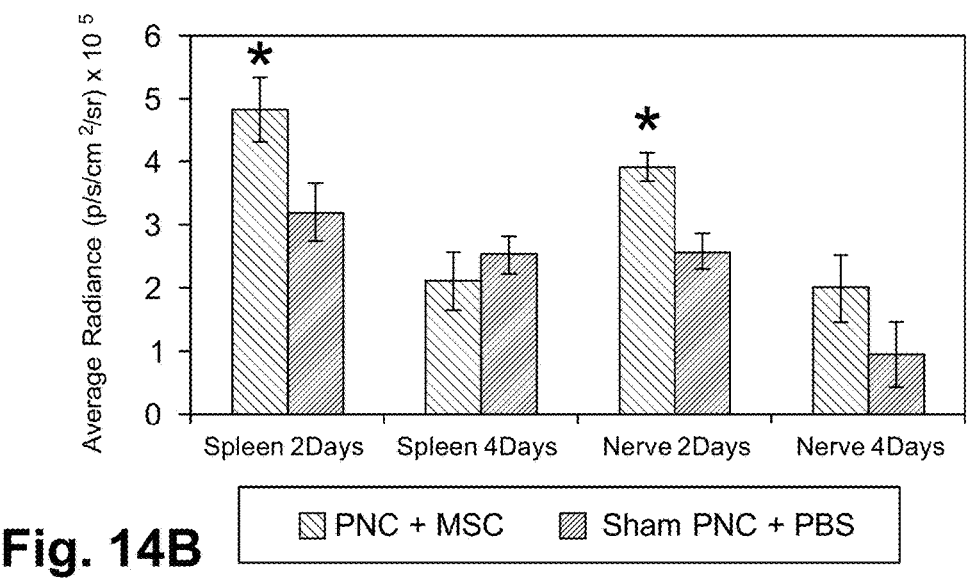

LPP was significantly reduced in PNC rats treated with PBS or control media compared to sham PNC, but not in those given IV MSCs or CCM (FIGS. 11A-B). EUS EMG frequency both at baseline and during LPP were significantly decreased in PNC rats treated with PBS or control media compared to sham PNC, but not in those given IV MSCs or CCM (FIGS. 12A-B). EUS EMG amplitude both at baseline and during LPP were significantly decreased in PNC rats treated with PBS or control media compared to sham PNC, but not in those given IV MSCs or CCM (FIGS. 13A-B). Ex vivo imaging showed significantly increased fluorescence in the pudendal nerve and spleen of PNC rats receiving IV MSC (FIGS. 14A-B).

From the above description, those skilled in the art will perceive improvements, changes and modifications. For example, it will be appreciated that therapeutically effective amounts of both bone marrow-derived MSCs and concentrated culture media of the present disclosure can be administered to a subject (e.g., via co-administration or sequentially). It will also be appreciated that the present disclosure can find use in a number of other applications, such as using the CCM as an animal feed supplement, as a food additive or dietary supplement, or as a cell culture medium (e.g., "re-used" to culture cells, particularly cells that are difficult to culture in vitro). Such improvements, changes, and modifications are within the skill of one in the art and are intended to be covered by the appended claims. All references cited herein and listed above are incorporated by reference in their entireties as needed and as discussed herein.

The following is claimed:

1. A method for treating a genitourinary disorder in a subject, said method comprising the steps of:
   culturing a population of bone marrow-derived mesenchymal stem cells (MSCs);
   obtaining an amount of a concentrated culture media from the cultured population of bone marrow-derived MSCs that is substantially free of any bone marrow-derived MSCs; and
   administering a therapeutically effective amount of the concentrated culture media to the subject.

2. The method of claim 1, wherein said culturing step further includes culturing the population of bone marrow-derived MSCs for a time and under conditions sufficient to promote paracrine factor secretion of extracellular proteins and cellular metabolites capable of supporting the growth of the population of bone marrow-derived MSCs.

3. The method of claim 1, wherein the culture media is concentrated at least about 10×.

4. The method of claim 1, wherein the culture media is concentrated at least about 50×.

5. The method of claim 1, wherein the therapeutically effective amount of the concentrated culture media is administered to the subject at or near a target location associated with the genitourinary disorder.

6. The method of claim 5, wherein the therapeutically effective amount of the concentrated culture media is administered to the subject via a periurethral injection.

7. The method of claim 1, wherein the genitourinary disorder is selected from the group consisting of urinary incontinence, stress urinary incontinence, overactive bladder, pelvic organ prolapse, interstitial cystitis, incontinence as a result of prostatectomy, fecal incontinence, and erectile dysfunction.

* * * * *